US012765757B2

(12) United States Patent
Yanuma

(10) Patent No.: US 12,765,757 B2
(45) Date of Patent: Oct. 20, 2026

(54) PUNCTURE DEVICE AND ENDOSCOPY SYSTEM

(71) Applicant: OLYMPUS MEDICAL SYSTEMS CORP., Tokyo (JP)

(72) Inventor: Yutaka Yanuma, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 296 days.

(21) Appl. No.: 18/523,426

(22) Filed: Nov. 29, 2023

(65) Prior Publication Data

US 2024/0180407 A1 Jun. 6, 2024

Related U.S. Application Data

(60) Provisional application No. 63/385,727, filed on Dec. 1, 2022.

(51) Int. Cl.

| | |
|---|---|
| ***A61B 17/34*** | (2006.01) |
| ***A61B 1/00*** | (2006.01) |
| ***A61B 1/018*** | (2006.01) |
| ***A61B 1/273*** | (2006.01) |

(52) U.S. Cl.

CPC .......... *A61B 1/018* (2013.01); *A61B 1/00042* (2022.02); *A61B 1/00128* (2013.01); *A61B 1/273* (2013.01)

(58) Field of Classification Search

CPC ....... A61B 17/34–3417; A61B 17/3472–3478; A61B 17/3496; A61B 1/018; A61B 1/005; A61B 1/273; A61B 1/2733; A61B 1/2736; A61B 10/0233; A61B 2010/045; A61M 25/0067

See application file for complete search history.

(56) References Cited

U.S. PATENT DOCUMENTS

| | | | | |
|---|---|---|---|---|
| 6,770,053 B2 * | 8/2004 | Scarfone | A61B 17/3496 | 604/117 |
| 2005/0090764 A1 * | 4/2005 | Wang | A61B 10/04 | 600/564 |
| 2013/0006144 A1 * | 1/2013 | Clancy | A61B 10/04 | 600/567 |
| 2016/0331358 A1 * | 11/2016 | Gordon | A61B 10/0233 | |
| 2021/0045720 A1 * | 2/2021 | Kadamus | A61B 10/0233 | |
| 2022/0176089 A1 | 6/2022 | Isayama | | |

* cited by examiner

*Primary Examiner* — Kathleen S Holwerda

(74) *Attorney, Agent, or Firm* — Schwegman Lundberg & Woessner, P.A.

(57) ABSTRACT

A puncture device according to an aspect of the present disclosure is a puncture device inserted into an endoscope channel, including: an outer sheath; an inner sheath inserted into the outer sheath; the inner sheath including; a coil sheath; and a needle tube located at a distal end of the coil sheath; a connecting portion connecting the needle tube and the coil sheath; and a cover covering the coil sheath and the connecting portion.

19 Claims, 22 Drawing Sheets

PUNCTURE DEVICE AND ENDOSCOPY SYSTEM

CROSS-REFERENCE TO RELATED APPLICATIONS

The present application claims priority based on U.S. Patent Provisional Application No. 63/385,727, filed in the United States on Dec. 1, 2022, the contents of which are incorporated herein by reference.

TECHNICAL FIELD

The present disclosure relates to a puncture device and an endoscopy system.

BACKGROUND

Endoscopic retrograde cholangiopancreatography (ERCP) is used for diagnosis of the bile duct, calculus retrieval, and stricture drainage by inserting a contrast agent, guide wire, and various catheters from the duodenum into the bile duct. In these procedures, an endoscope capable of ultrasonic observation and a puncture device that can be inserted through a treatment instrument channel of the endoscope are used.

As shown in US Patent Application Publication No. 2022/0176089 (Patent Document 1), the puncture device used for these procedures have flexibility to be largely curved to a position where the duodenal papilla located on the side of the endoscope can be punctured. In addition, the puncture device has rigidity to allow a straight puncture into the duodenal papilla in the direction intended by the operator.

SUMMARY

The present disclosure provides a puncture device that is both flexible and rigid, can be easily bent to the position intended by the operator, and can be easily operated in the direction intended by the operator, and an endoscopy system comprising the puncture device. In an example, a puncture device inserted into an endoscope channel, including: an outer sheath; an inner sheath inserted into the outer sheath; the inner sheath including; a coil sheath; and a needle tube located at a distal end of the coil sheath; a connecting portion connecting the needle tube and the coil sheath; and a cover covering the coil sheath and the connecting portion.

DETAILED DESCRIPTION

First Embodiment

Figure 1:
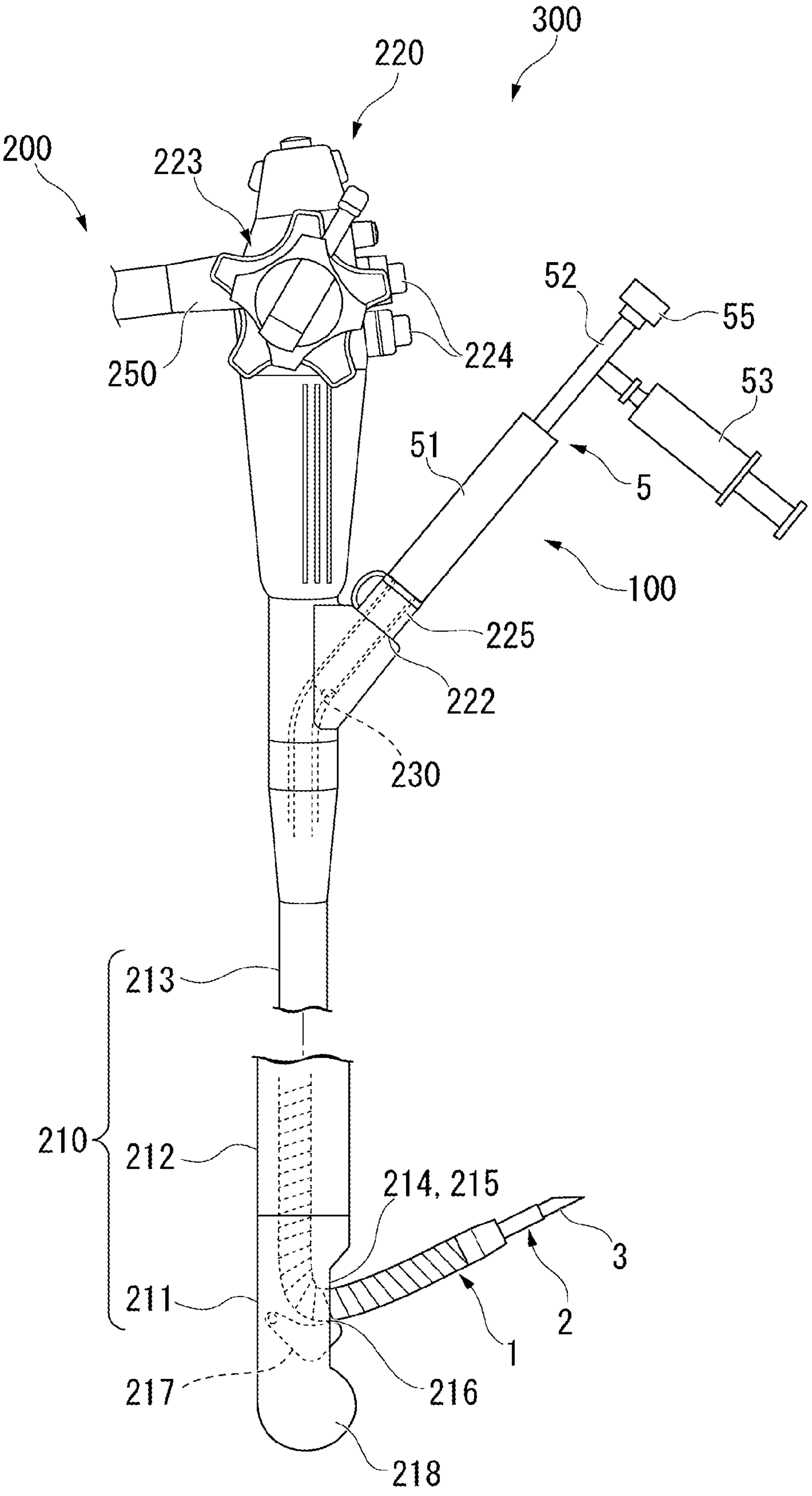
FIG. 1 is an overall view of an endoscopy system according to the embodiment.

A first embodiment of the present disclosure will be described with reference to FIGS. 1 to 19. FIG. 1 is an overall view of an endoscope treatment system 300 according to this embodiment.

[Endoscope Treatment System 300]

The endoscope treatment system 300 includes a puncture device 100 and an endoscope 200. The puncture device 100 is used by being inserted into endoscope 200.

[Endoscope 200]

The endoscope 200 is a flexible endoscope on the side viewing side capable of optical observation and ultrasonic observation. The endoscope 200 includes an elongated insertion portion 210, an operation portion 220 provided at the proximal end of the insertion portion 210, and a universal cord 250 extending from the operation portion 220. Here, the endoscope 200 may be a direct-view flexible endoscope.

The insertion portion 210 includes a distal end portion 211 provided at the distal end, a bendable bending portion 212 provided at the proximal side of the distal end portion 211, and a flexible tube portion 213 provided at the proximal side of the bending portion 212. The insertion portion 210 is formed with a treatment instrument channel 230 through which an endoscopic treatment instrument such as the puncture device 100 can be inserted.

A light guide 214, an optical observation portion 215 having an imaging device such as a CCD, and a distal end opening 216 communicating with the treatment instrument channel 230 are provided on the side surface of the distal end portion 211.

A raising base 217 is provided near the distal end opening 216 of the distal end portion 211. A proximal portion of the raising base 217 is rotatably supported by the distal end portion 211. A raising base operation wire (not shown) fixed to the distal end of the raising base 217 extends through the insertion portion 210 to the operation portion 220.

An ultrasonic transducer 218 is provided at the distal end of the distal end portion 211. Here, the ultrasonic transducer 218 may be provided closer to the proximal side than the distal opening 216.

The bending portion 212 can be bent vertically and horizontally. The distal end of the operation wire is fixed to the distal end side of the bending portion 212. The operation wire extends through the insertion portion 210 to the operation portion 220.

The operation unit 220 is provided with a knob 223 for operating the operation wire and the raising base operation wire, and a switch 224 for operating the optical observation unit 215 and the like. The operator can bend the bending portion 212 in a desired direction by operating the knob 223.

The operation portion 220 is provided with a forceps opening (base end opening) 222 that communicates with the treatment instrument channel 230. The operator can insert an endoscopic treatment tool such as the puncture device 100 through the forceps port 222. A forceps plug 225 is attached to the forceps port 222 to prevent leakage of bodily fluids.

The universal cord 250 connects the endoscope 200 to the video controller. An imaging signal imaged by the optical observation unit 215 is transmitted to the image control device via the universal code 250.

[Puncture Device 100]

Figure 2:
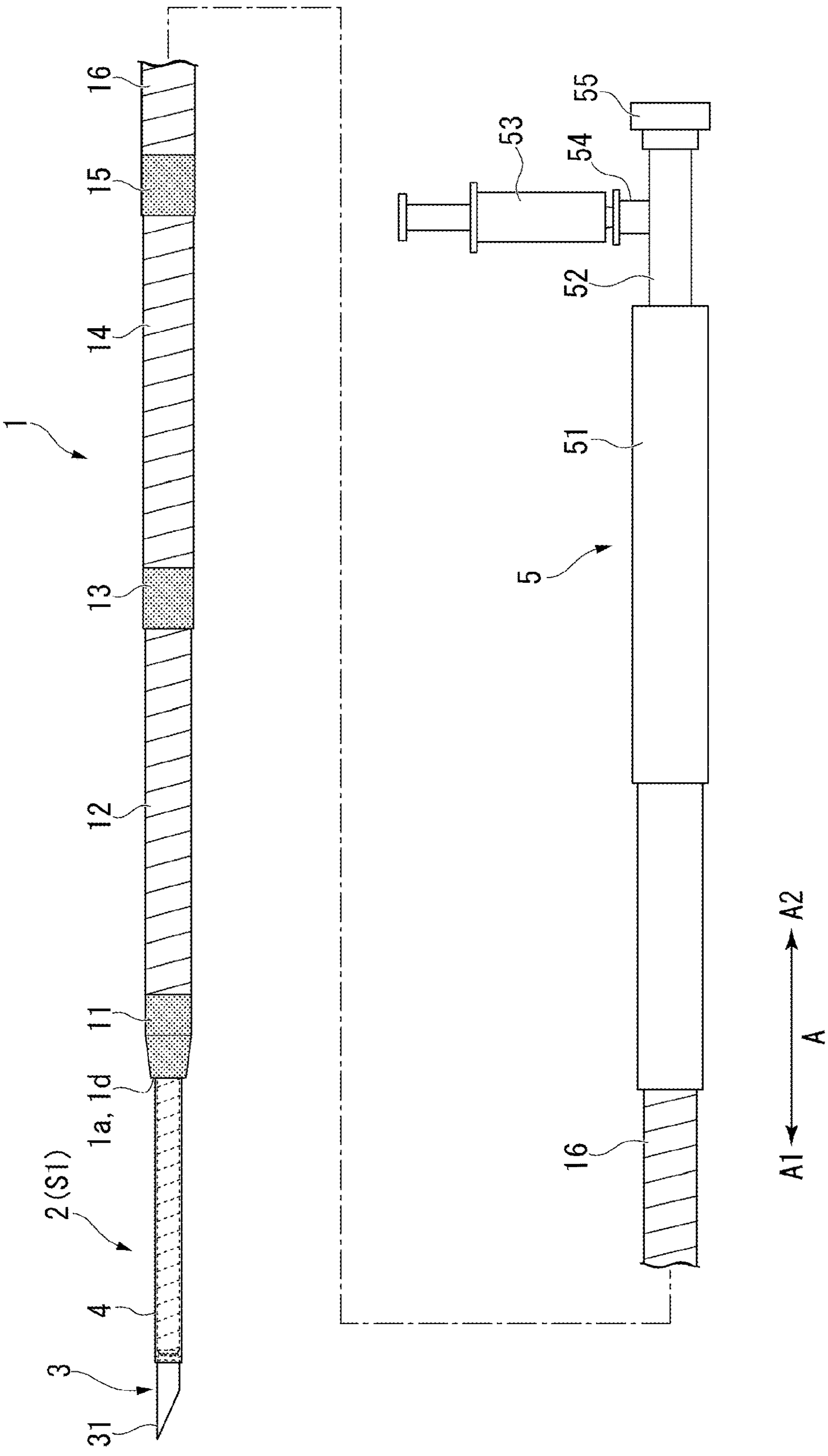
FIG. 2 is an overall view showing a puncture device of the endoscope treatment system.

FIG. 2 is an overall view showing the puncture device 100.

The puncture device 100 includes an outer sheath 1, an inner sheath 2, a needle tube 3, a cover 4, and an operation portion 5.

In the following description, the side inserted into the lumen of the patient P in the longitudinal direction A of the puncture device 100 is defined as the "distal end side (distal side) A1", and the side of the operation unit 5 is defined as the "proximal end side (proximal side) A2".

Figure 3:
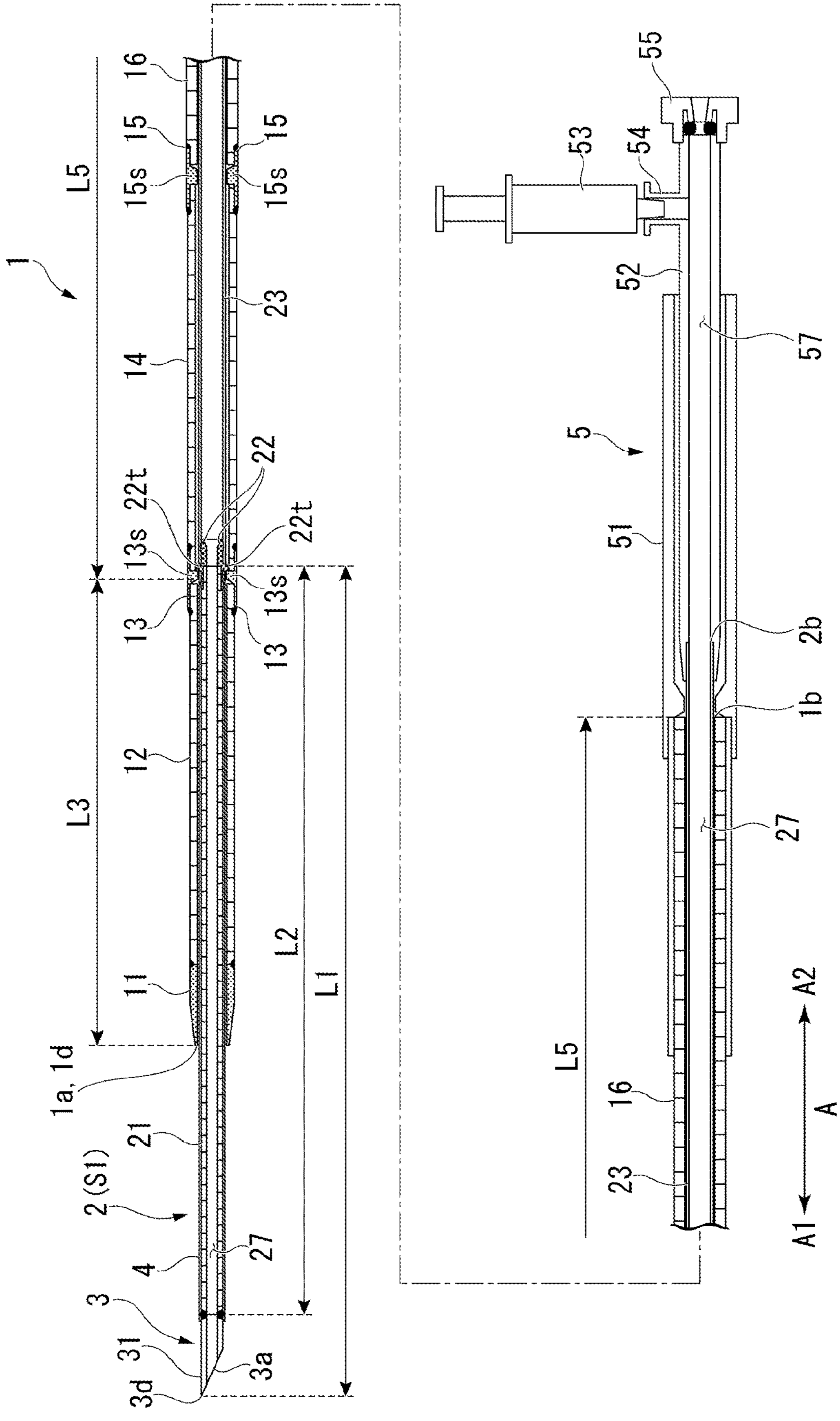
FIG. 3 is a cross-sectional view of the puncture device.

FIG. 3 is a cross-sectional view of the puncture device 100.

The outer sheath 1 is a long tubular member that can be inserted through the treatment instrument channel 230 of the endoscope 200. The outer sheath 1 has a distal end portion 11, a distal coil sheath 12, a first connecting portion 13, an intermediate coil sheath 14, a second connecting portion 15 and a proximal coil sheath 16. The distal portion 11, the distal coil sheath 12, the first connecting portion 13, the intermediate coil sheath 14, the second connecting portion 15, and the proximal coil sheath 16 are arranged from the distal side A1 toward the proximal side A2. The outer sheath 1 has an internal space (lumen) 17 communicating with a distal opening 1 a provided at the distal end of the distal portion 11 and a proximal opening 1*b* provided at the proximal end of the proximal coil sheath 16.

The distal end (protective member) 11 is a rigid tube-shaped member provided at the distal end of the outer sheath 1. The distal end portion (protective member) 11 may be a metal member or a plastic member reinforced with glass or carbon. A distal end opening 1*a* communicating with the internal space 17 is formed at the distal end Id of the distal end portion 11. The proximal end of the distal end portion 11 is attached to the distal end of the distal coil sheath 12.

The distal end coil sheath 12 is a coil sheath formed by spirally winding a metal wire. The distal coil sheath 12 is made of a thin, flat wire and is easily bendable compared to the proximal coil sheath 16.

The first connecting portion 13 connects the distal end coil sheath 12 and the intermediate coil sheath 14. The first connecting portion 13 has a first stopper 13*s*. The first stopper 13 *s* is a protrusion projecting radially inward in the internal space 17.

The intermediate coil sheath 14 is a coil sheath formed by spirally winding a metal wire. The intermediate coil sheath 14 has an inner diameter larger than that of the distal coil sheath 12, and a proximal end connecting portion 22 provided with a protrusion 22*t* of the inner sheath 2, which will be described later, can be inserted therethrough.

The second connecting portion 15 connects the intermediate coil sheath 14 and the proximal end coil sheath 16. The second connecting portion 15 has a second stopper 15*s*. The second stopper 15 *s* is a convex portion that protrudes radially inward in the internal space 17.

The proximal end coil sheath 16 is a coil sheath formed by spirally winding a metal wire. A proximal end of the proximal coil sheath 16 is connected to the operation portion 5. The proximal end coil sheath 16 is formed of a thicker flat wire than the distal end coil sheath 12, and facilitates the transmission of forward and backward forces. Also, the proximal end coil sheath 16 is difficult to extend in the longitudinal direction A.

The inner sheath 2 is a long tubular member that can be inserted into the inner space 17 of the outer sheath 1. The inner sheath 2 has a coil sheath 21, a proximal end connecting portion 22 and a proximal sheath 23. The coil sheath 21, the proximal end connecting portion 22 and the proximal sheath 23 are arranged from the distal side A1 toward the proximal side A2. The inner sheath 2 has an internal space (guide wire lumen) 27 communicating with a distal opening 2 a provided at the distal end of the coil sheath 21 and a proximal opening 2*b* provided at the proximal end of the proximal sheath 23.

Figure 4:
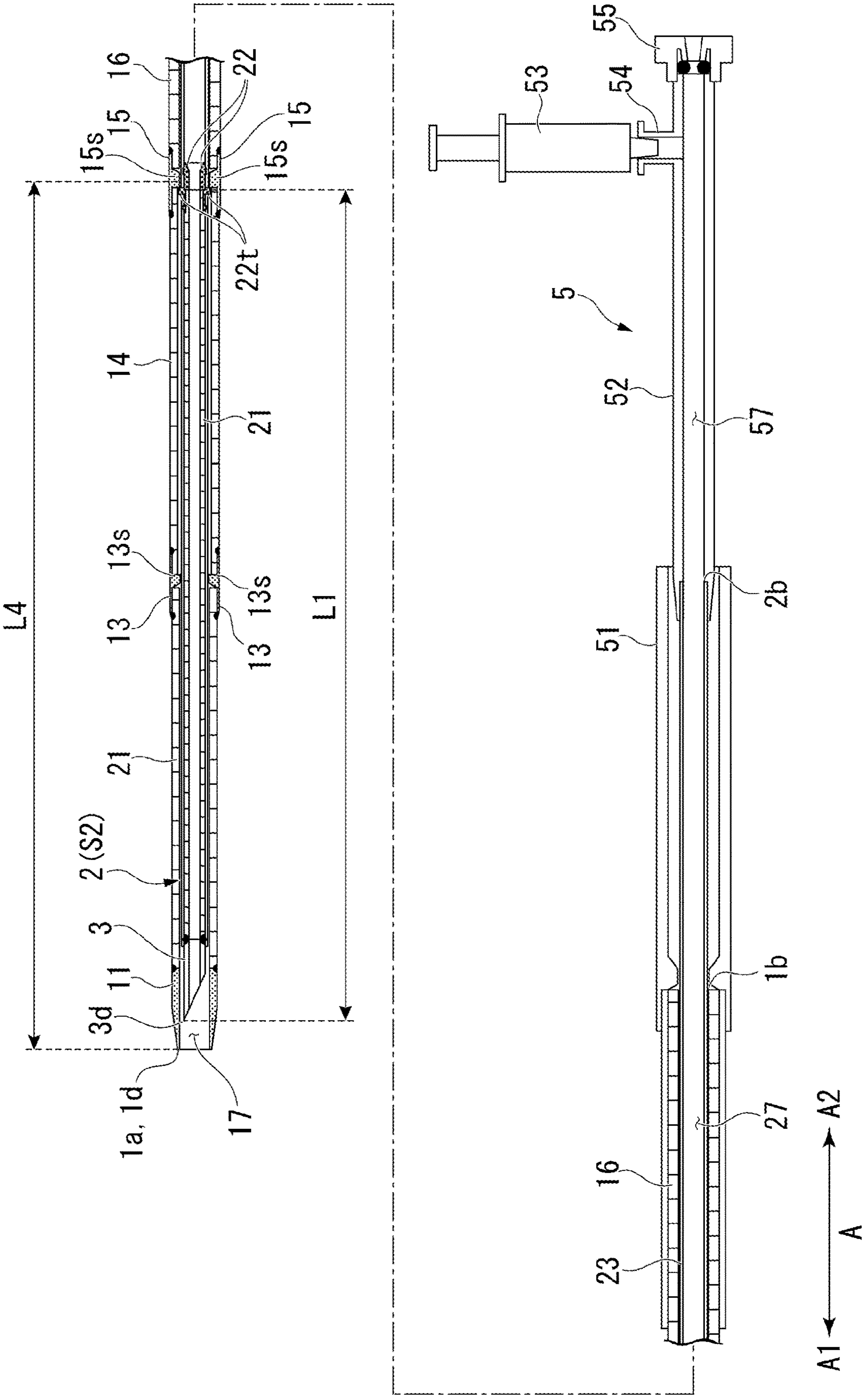
FIG. 4 is a cross-sectional view of the puncture device.

FIG. 4 is a cross-sectional view of the puncture device 100.

The inner sheath 2 is inserted through the inner space 17 of the outer sheath 1. Specifically, the inner sheath 2 passes through the distal end opening 1*a* and the proximal end opening 1*b* of the outer sheath 1 and is inserted into the inner space 17 of the outer sheath 1 so as to be relatively movable. The outer diameter of the inner sheath 2 is smaller than the inner diameter of the inner space 17 of the outer sheath 1.

The coil sheath 21 is a coil sheath formed by spirally winding a metal wire. The distal end coil sheath 12 is made of a flat wire and is easily bendable.

The proximal end connecting portion 22 connects the coil sheath 21 and the proximal sheath 23. The proximal end connecting portion 22 has a protrusion 22*t*. The protrusion 22*t* is a convex portion which protrudes toward the outer side of a radial direction.

The proximal sheath 23 is a sheath made of a highly rigid resin such as PEEK. The proximal end of the proximal sheath 23 is connected to the operation portion 5. The inner diameter of the proximal sheath 23 is larger than the inner diameter of the coil sheath 21. The length of the proximal sheath 23 in the longitudinal direction A is longer than the length of the coil sheath 21 in the longitudinal direction A.

Figure 5:
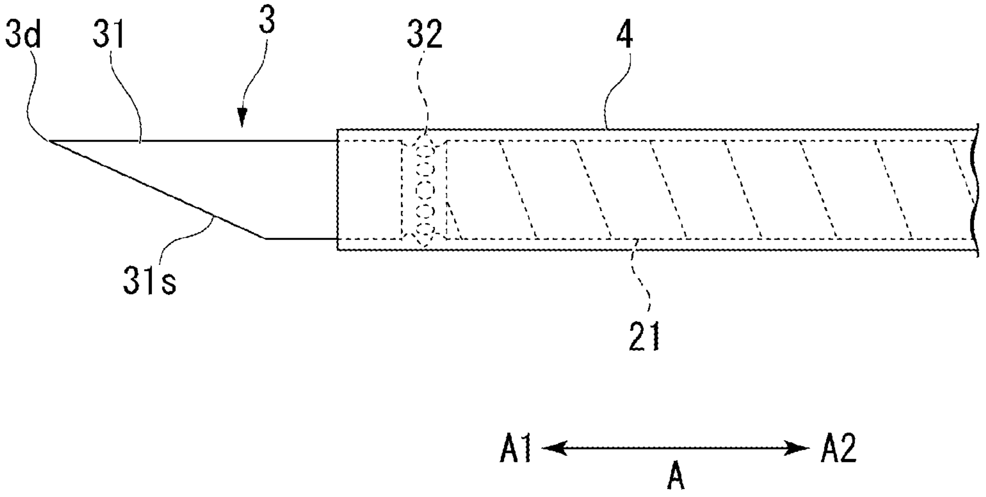
FIG. 5 is a diagram showing a needle tube and a cover of the puncture device.

FIG. 5 is a diagram showing the needle tube 3 and the cover 4.

The needle tube 3 is a hollow member made of metal and having a sharp portion 31 on the distal end side A1. The needle tube 3 is attached to the distal end of the inner sheath 2 and is inserted through the inner space 17 of the outer sheath 1 together with the inner sheath 2.

Figure 6:
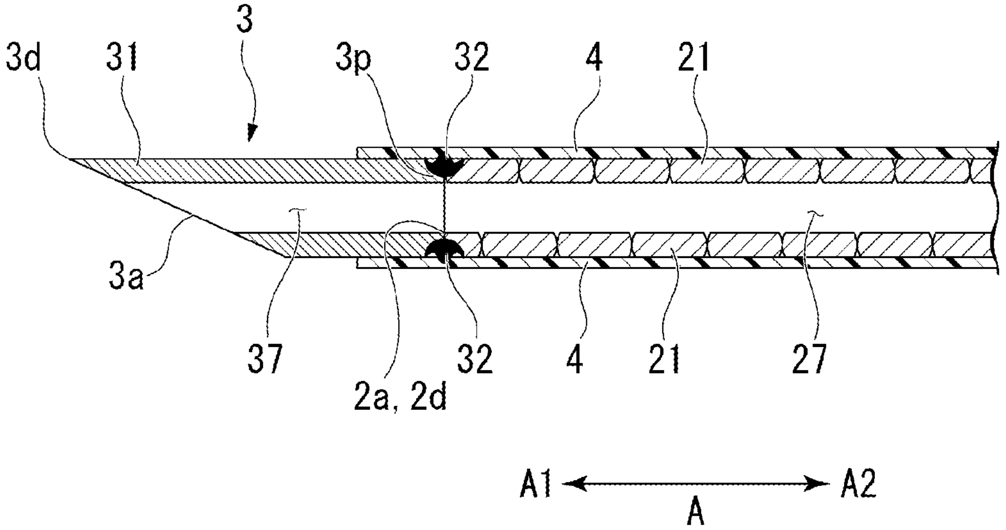
FIG. 6 is a sectional view of the needle tube and the cover.

FIG. 6 is a cross-sectional view of the needle tube 3 and the cover 4.

A proximal end 3*p* of the needle tube 3 is connected to a distal end 2*d* of the coil sheath 21 via a distal end connecting portion 32. The internal space 37 of the needle tube 3 communicates with the distal end opening 3*a* on the distal end side A1, and communicates with the internal space 27 of the inner sheath 2 via the distal end opening 2*a* on the proximal side A2.

The sharp portion 31 is formed in a blade shape having an inclined surface 31*s* inclined with respect to the longitudinal direction A. A distal end opening 3*a* is formed in the inclined surface 31*s*. Here, the shape of the sharp portion 31 may be another shape such as a double-headed needle shape.

The distal connecting portion 32 is a portion where the proximal end 3*p* of the needle tube 3 and the distal end 2*d* of the coil sheath 21 are connected by, for example, laser welding. The distal end connecting portion 32 has a stepped portion and unevenness due to a connection processing such as laser welding at the connecting portion between the needle tube 3 and the coil sheath 21. For example, when the distal end connecting portion 32 is connected by laser welding, the distal end connecting portion 32 has uneven laser welding traces.

Figure 7:
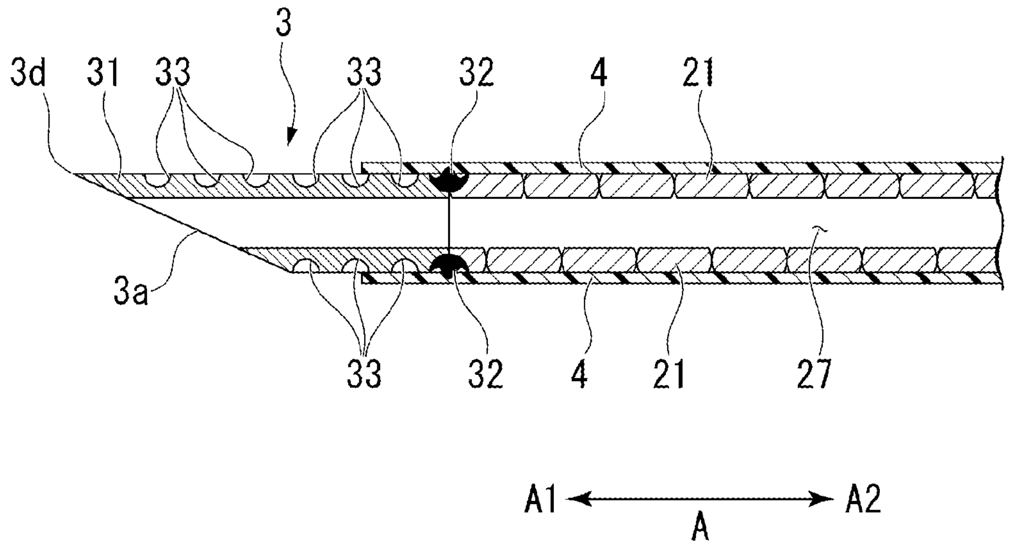
FIG. 7 is a cross-sectional view of the needle tube having dimples and the cover.

FIG. 7 is a cross-sectional view of the needle tube 3 having the dimple 33 and the cover 4.

The needle tube 3 may have one or more dimples (grooves, concave portions) 33 that are recessed on the outer surface. In this case, ultrasonic waves are more likely to be reflected, and the position of the needle can be easily confirmed on the ultrasonic image.

The cover 4 is a tube provided on a portion of the proximal side A2 of the needle tube 3 and the outer peripheral portion of the coil sheath 21, and is, for example, a heat-shrinkable tube. The cover 4 keeps the inner space 27 of the coil sheath 21 watertight. The cover 4 is provided straddling the distal end connecting portion 32. Specifically, the cover 4 is provided from the needle tube 3 on the distal side A1 of the distal connecting portion 32 to the coil sheath 21 on the proximal side A2 of the distal connecting portion 32. The cover 4 is hooked (engaged) on steps and irregularities formed due to connection processing such as laser welding in the distal connecting portion 32. Therefore, the cover 4 is firmly fixed to the distal connecting portion 32 and is less likely to slip off the distal connecting portion 32.

When the needle tube 3 has dimples 33, the cover 4 may be hooked (engaged) on the dimples 33 as shown in FIG. 7. The cover 4 is firmly fixed to the dimple 33 in addition to the distal end connecting portion 32 and is not easily displaced from the distal end connecting portion 32. Specifically, when the needle tube 3 is punctured into the tissue such as the bile duct BD toward the distal side A1, the cover 4 may receive a force to move toward the proximal side A2 due to the reaction received from the tissue. The distal connecting portion 32 restricts the movement of the cover 4 to the proximal side A2. Similarly, the dimple 33 restricts the movement of the cover 4 toward the proximal side A2.

Figure 8:
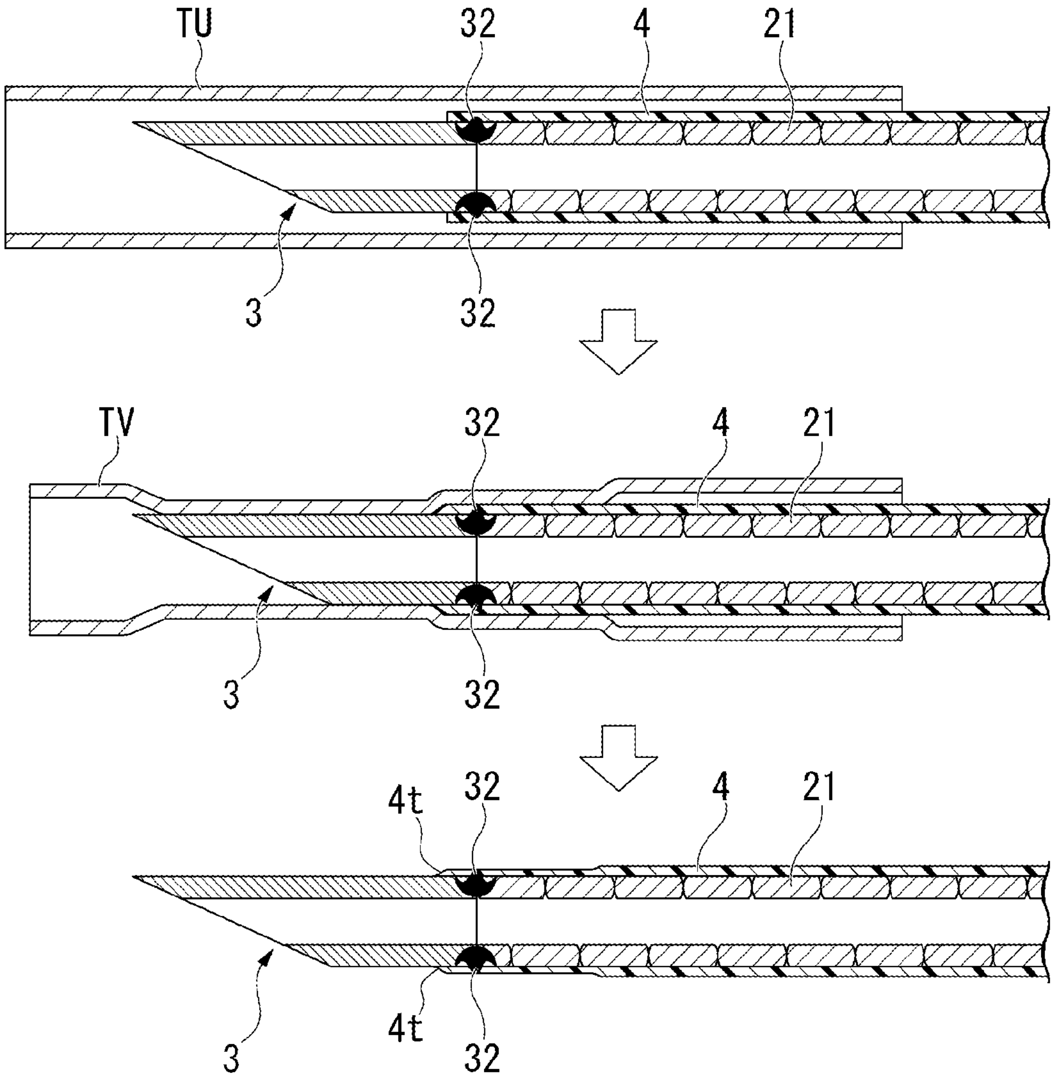
FIG. 8 is a diagram showing an example of a method of melting and attaching the cover.

FIG. 8 is a diagram showing an example of a method of melting the cover 4 and attaching it.

The worker covers the cover 4 with a heat-shrinkable tube TU for processing, which has a heat resistance temperature higher than the melting temperature of the cover 4. An operator shrinks the heat-shrinkable tube TU for processing with heat equal to or higher than the melting temperature of the cover 4, and removes the heat-shrinkable tube TU for processing when at least a part of the cover 4 melts. As a result, the front end or the entire length of the cover 4 is melted while being subjected to the contraction pressure of the heat-shrinkable tube TU for processing, so that the melted cover 4 can melt into every corner of the steps and unevenness of the front end connecting portion 32. Therefore, the cover 4 is firmly fixed by the distal connecting portion 32 and is less likely to slip off the distal connecting portion 32.

Figure 9:
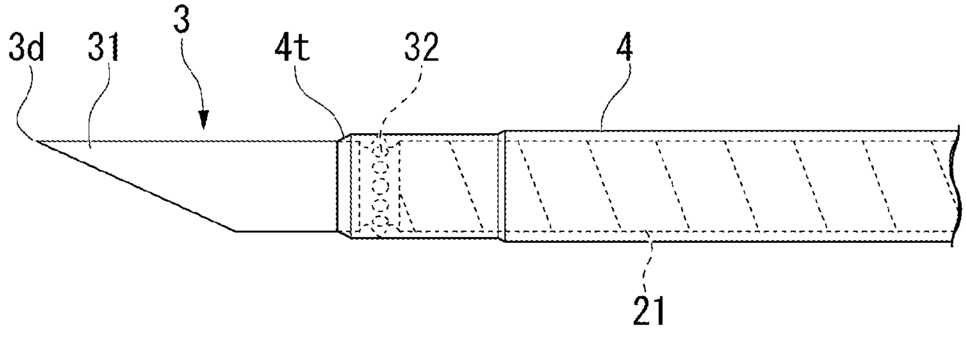
FIG. 9 is a diagram showing the cover attached by melting.

FIG. 9 is a diagram showing the cover 4 attached by melting.

The cover 4 attached by melting forms a tapered portion 4*t* at the distal end of the cover 4 by melting. Therefore, the puncture performance of the puncture device 100 is improved.

The operation portion 5 includes a first operating member 51 connected to the proximal end of the outer sheath 1, a second operating member 52 connected to the proximal end of the inner sheath 2, and a syringe 53 connected to the second operating member 52.

The second operating member 52 is formed in a tubular shape. The internal space (lumen) 57 of the second operating member 52 communicates with the internal space (guidewire lumen) 27 of the inner sheath 2 via the proximal end opening 2*b*. The second operating member 52 has an opening 54 to which the syringe 53 is connected and a guide wire port 55 through which the guide wire GW is inserted.

The opening 54 is an opening to which the syringe 53 is attached and communicates with the internal space 57. A fluid such as degassed water, physiological saline, or a contrast agent supplied from the syringe 53 passes through the internal space 27 of the inner sheath 2 and the internal space 37 of the needle tube 3 and flows out from the distal end opening 3*a* of the needle tube 3.

Figure 10:
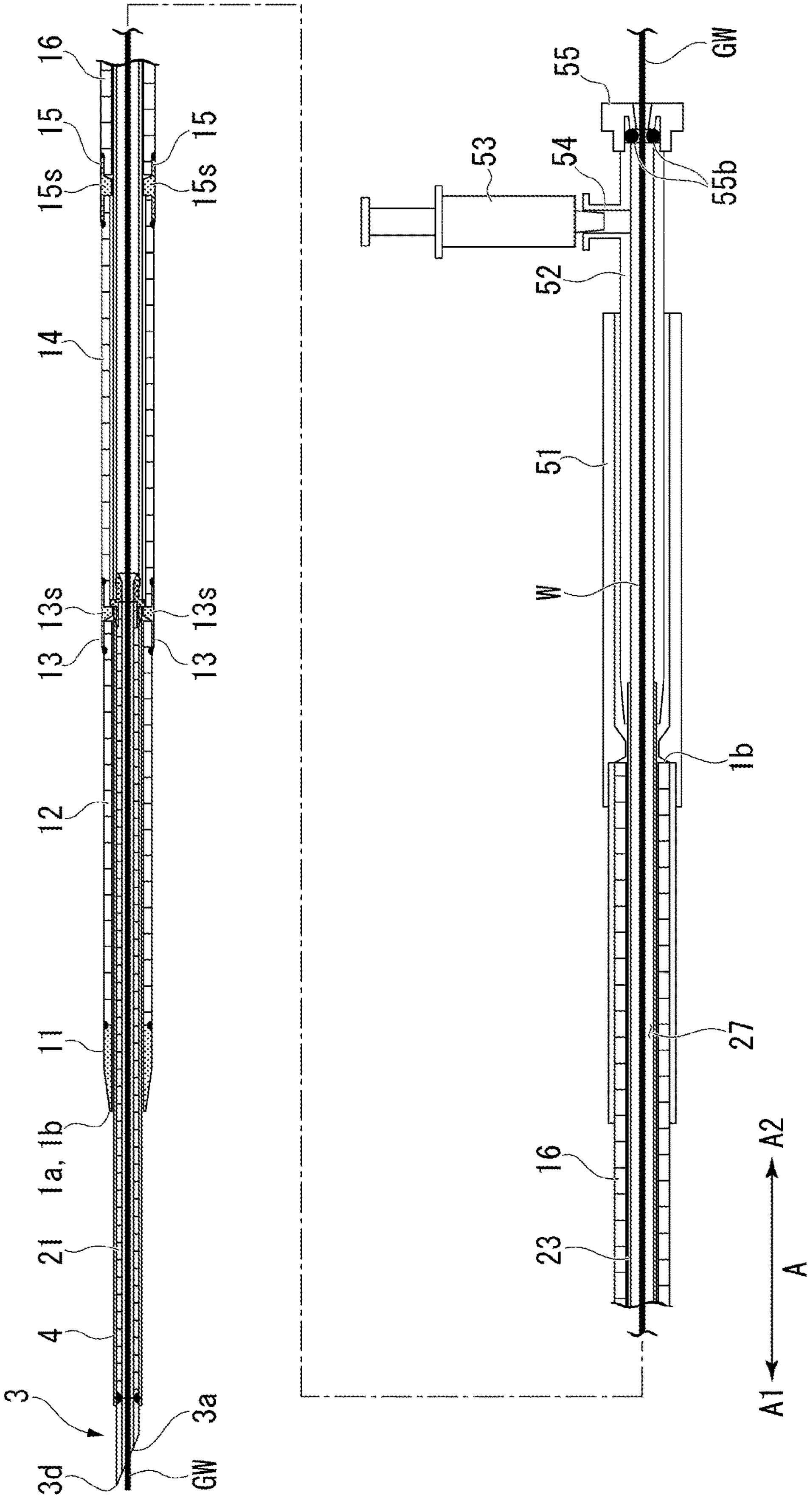
FIG. 10 is a cross-sectional view of the puncture device with a guidewire inserted.

FIG. 10 is a cross-sectional view of the puncture device 100 with the guidewire GW inserted.

The guidewire port 55 is an opening through which the guidewire GW is inserted. The guide wire GW inserted from the guide wire port 55 passes through the inner space 27 of the inner sheath 2 and the inner space 37 of the needle tube 3 and protrudes from the distal end opening 3*a* of the needle tube 3. A watertight ring 55*b* is attached to the guidewire port 55. When the guidewire GW is inserted from the guidewire port 55, the watertight ring 55*b* is loosened. When the fluid is fed from the syringe 53, the watertight ring 55*b* is squeezed to keep the internal space 57 of the second operating member 52 watertight.

The operator can advance and retreat the inner sheath 2 with respect to the outer sheath 1 by advancing and retreating the second operating member 52 with respect to the first operating member 51 in the longitudinal direction A. The movement range of the inner sheath 2 with respect to the outer sheath 1 is restricted by the first stopper 13*s* and the second stopper 15*s*.

The inner sheath 2 shown in FIG. 3 is arranged at the first position S1, which is the most (fully) advanced with respect to the outer sheath 1. The engagement of the protrusion 22*t* of the inner sheath 2 with the first stopper 13*s* of the outer sheath 1 restricts the forward movement of the inner sheath 2 relative to the outer sheath 1.

A first length L1 in the longitudinal direction A from the distal end 3d of the needle tube 3 to the protrusion 22t of the inner sheath 2 is longer than a third length L3 in the longitudinal direction A from the distal end Id of the outer sheath 1 to the first stopper 13s (L1>L3). Also, the second length L2 in the longitudinal direction A from the distal end 2d of the inner sheath 2 to the protrusion 22t of the inner sheath 2 is longer than the third length L3 (L2>L3). Therefore, when the inner sheath 2 is arranged at the first position S<b>1 that is the most (fully) advanced with respect to the outer sheath 1, at least part of the needle tube 3 and the coil sheath 21 protrude from the distal end opening 1a of the outer sheath 1.

The inner sheath 2 shown in FIG. 4 is arranged at the second position S2, which is the most (fully) retracted with respect to the outer sheath 1. The protrusion 22t of the inner sheath 2 is engaged with the second stopper 15s of the outer sheath 1, thereby restricting the retraction of the inner sheath 2 with respect to the outer sheath 1.

A first length L1 in the longitudinal direction A from the distal end 3d of the needle tube 3 to the protrusion 22t of the inner sheath 2 is shorter than a fourth length L4 in the longitudinal direction A from the distal end 1d of the outer sheath 1 to the second stopper 15s (L1<L4). Therefore, when the inner sheath 2 is arranged at the second position S2 that is the (fully) backward with respect to the outer sheath 1, the distal end 3d of the needle tube 3 is accommodated in the inner space 17 of the outer sheath 1. At this time, the distal end 3d of the needle tube 3 is arranged at a position surrounded by the distal end portion 11.

[Operation of Endoscope Treatment System 300]

Next, operations and effects of the endoscope treatment system 300 according to this embodiment will be described with reference to FIGS. 11 to 19. Specifically, a procedure for treating the bile duct BD by endoscopic retrograde cholangiopancreatography (ERCP) is described. Here, the procedure described below is based on the procedure described in US Patent Application Publication No. 2022/0176089.

<Step S1: Endoscope Insertion Step>

In step S1, the operator inserts the insertion portion 210 of the endoscope 200 into the patient's lumen through a natural opening such as the mouth. The operator bends the bending portion 212 by operating the operation portion 220, as necessary. The operator inserts the distal end portion 211 of the endoscope 200 to the vicinity of the duodenal papilla.

<Step S2: Endoscope Positioning Step>

The operator adjusts the position of the distal end portion 211 of the endoscope 200 so that the duodenal papilla falls within the imaging range of the optical observation portion 215 of the endoscope 200 in step S2. The operator adjusts the position of the distal end portion 211 by appropriately combining forward/backward operation, bending operation, twisting operation, and the like of the endoscope 200.

<Step S3: Water Supply Step>

Figure 14:
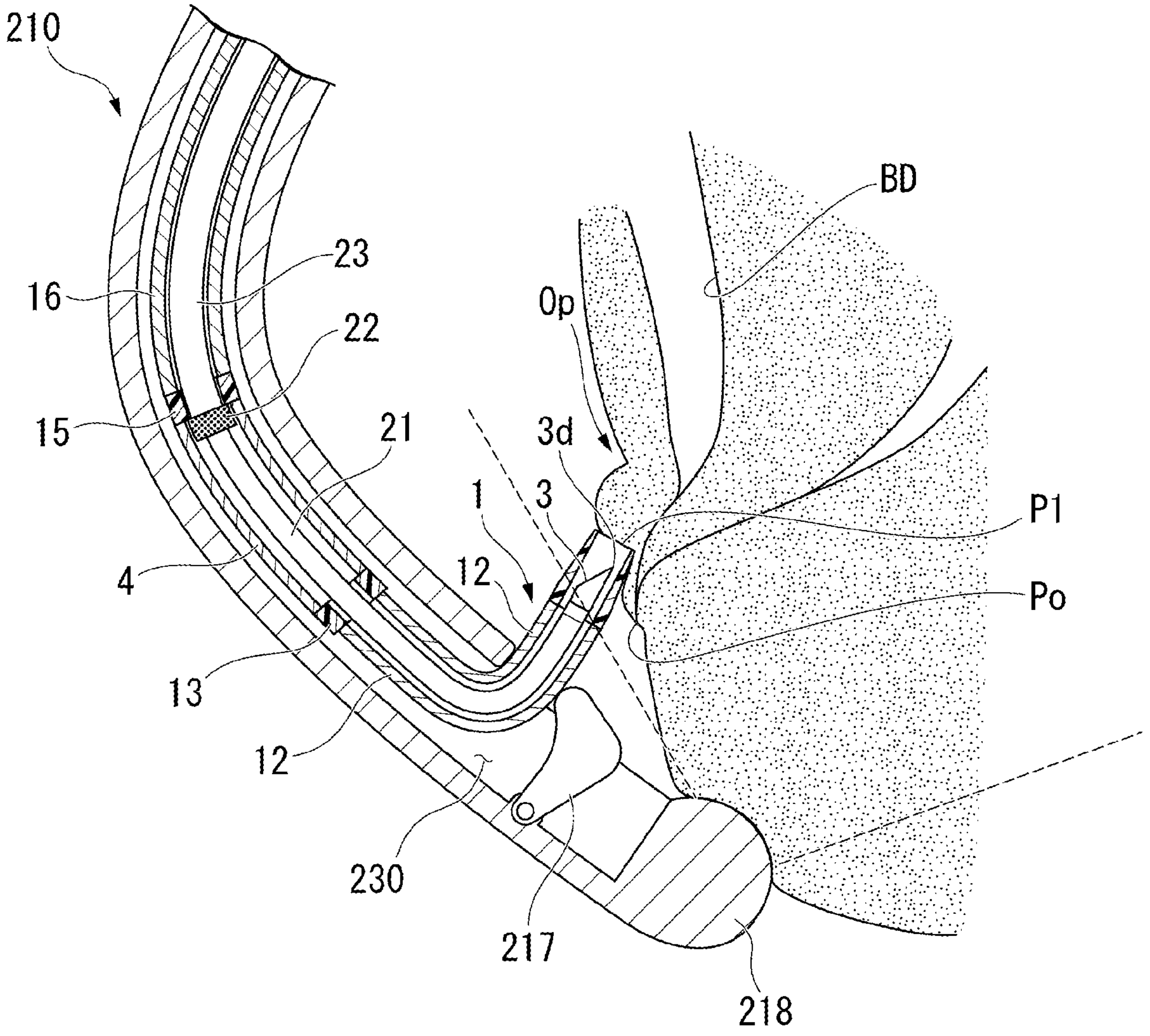
FIG. 14 is a cross-sectional view of the distal end portion of the puncture device with the distal end position adjusted.

Next, in step S3, the operator supplies water into the duodenum and causes the water to accumulate in the region of the duodenum where the distal end portion 211 of the endoscope 200 is located. After storing the water, the operator activates the ultrasonic transducer 218 to obtain an ultrasonic image, and confirms that the bile duct BD and pancreatic duct can be visualized. The operator may visualize the bile duct BD and pancreatic duct with ultrasound by pressing the ultrasonic transducer 218 directly against the duodenal mucosa as shown in FIG. 14 without supplying water.

<Step S4: Puncture Device Alignment Step>

Figure 11:
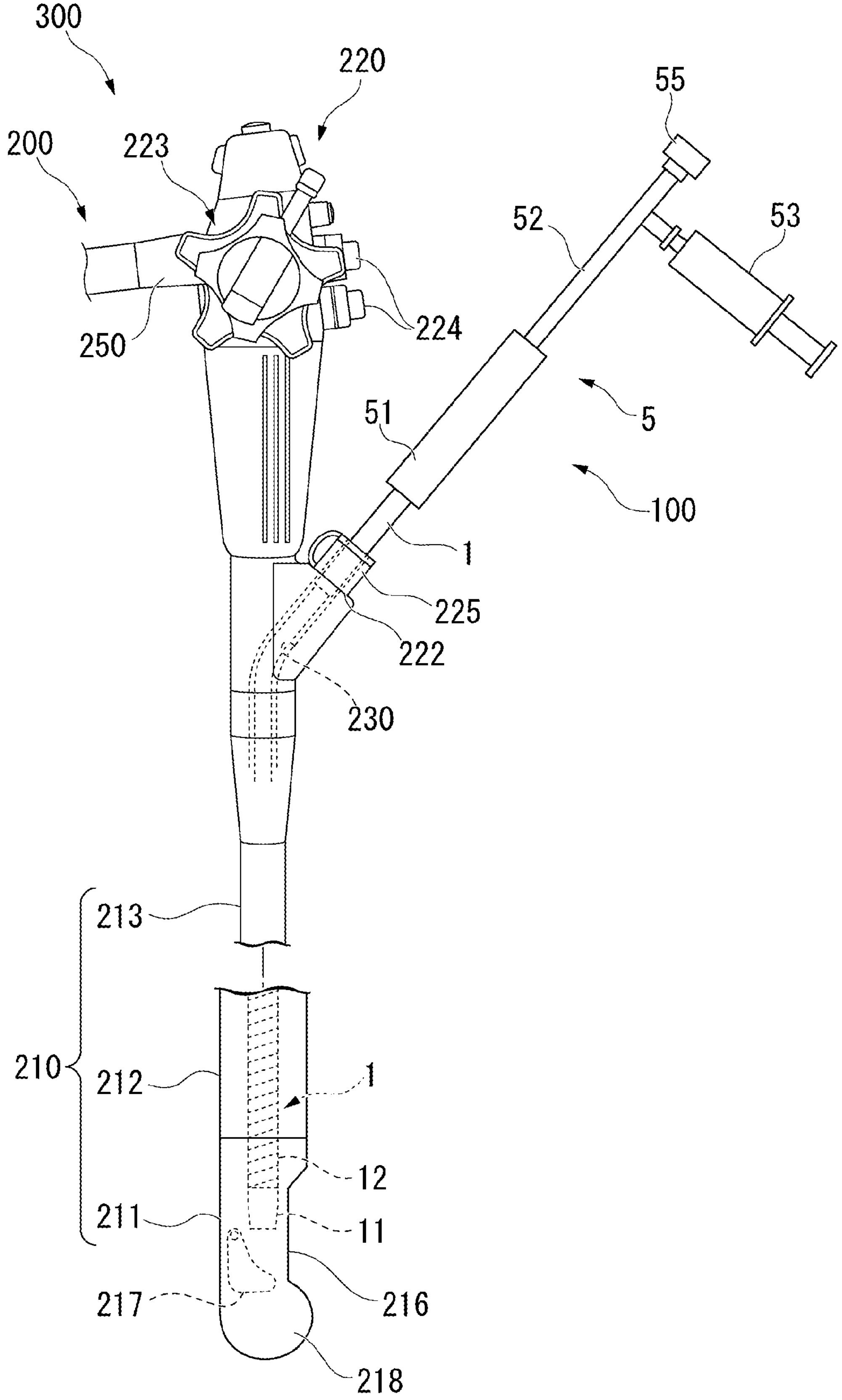
FIG. 11 is a diagram showing the puncture device inserted into an endoscope.

FIG. 11 is a diagram showing the puncture device 100 inserted into the endoscope 200.

Figure 12:
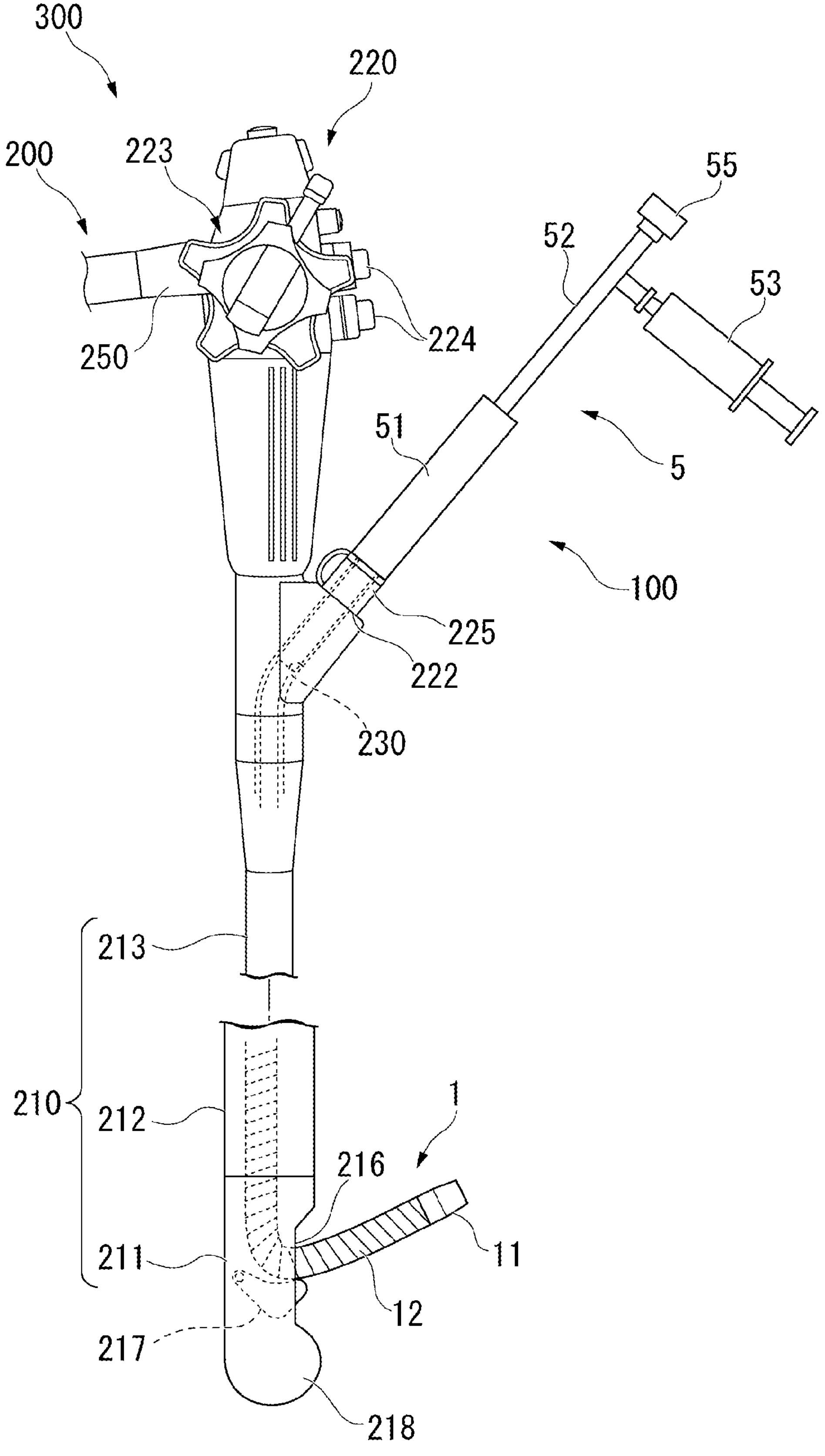
FIG. 12 is a view showing the puncture device with the outer sheath protruding.

Next, in step S4, the operator inserts the puncture device 100 into the treatment instrument channel 230 through the forceps opening (base end opening) 222 of the endoscope 200. The operator causes the distal end portion of the outer sheath 1 to protrude from the distal opening 216 as shown in FIG. 12. The operator operates endoscope 200 and puncture device 100 to position distal end portion 11 of outer sheath 1 within the field of view of optical observation portion 215. The operator operates the raising base 217, as necessary.

FIG. 12 is a diagram showing the puncture device 100 with the outer sheath 1 protruding.

The amount of protrusion of the outer sheath 1 with respect to the distal end opening 216 of the endoscope 200 is limited to a range in which the outer sheath 1 can be advanced with respect to the treatment instrument channel 230 of the endoscope 200. In the puncture device 100 shown in FIG. 12, the outer sheath 1 is inserted longest into the treatment instrument channel 230 and protrudes the farthest from the distal end opening 216 of the endoscope 200.

Figure 13:
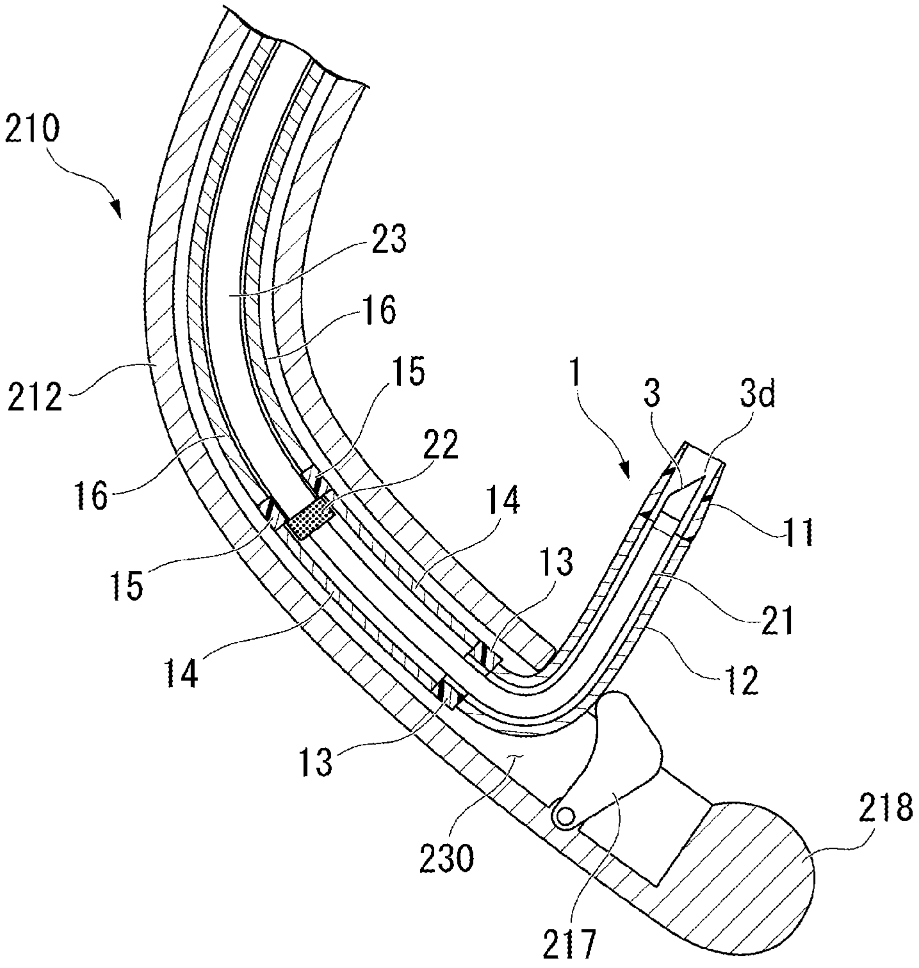
FIG. 13 is a cross-sectional view of the distal end portion of the puncture device in FIG. 12.

FIG. 13 is a cross-sectional view of the distal end portion of puncture device 100 in FIG. 12.

A fifth length L5 (see FIG. 3) from the first stopper 13s of the outer sheath 1 to the base end opening 1b of the outer sheath 1 is shorter than the length of the treatment instrument channel 230 of the endoscope 200. Therefore, when the outer sheath 1 is inserted into the treatment instrument channel 230 for the longest length as shown in FIG. 12, the first connecting portion 13 including the first stopper 13s is positioned inside the treatment instrument channel 230 as shown in FIG. 13. That is, even when the outer sheath 1 protrudes most (fully) from the distal end opening 216, the first connecting portion 13, which is a hard member, does not protrude from the distal end opening 216.

Since the distal end coil sheath 12, which is flexible regardless of the amount of protrusion of the outer sheath 1, is inserted near the distal end opening 216, the operator can easily adjust the position and orientation of the distal end portion 11 of the outer sheath 1 using the raising base 217. Further, even when the distal end coil sheath 12, which tends to bend, is greatly bent by the raising base 217, the distal end coil sheath 12 is less prone to bending.

The maximum amount of protrusion of the outer sheath 1 protruding from the distal end opening 216 may be 15 mm or more, and 25 mm or more.

FIG. 14 is a cross-sectional view of the distal end portion of the puncture device 100 whose distal end position has been adjusted.

Next, the operator determines the position P1 for puncturing the duodenal papilla with the needle tube 3 while viewing the ultrasonic image from the ultrasonic transducer 218. The operator adjusts the position P1 so that the position P1 is within the range of the oral protuberance Op and does not overlap with the natural opening Po. Next, the operator brings the distal end Id of the outer sheath 1 into contact with the position P1. At this point, the distal end 3d of the needle tube 3 is still housed in the inner space 17 of the outer sheath 1. As shown in FIG. Since the needle tube 3 is surrounded and protected by the hard distal end portion 11, even if the raising base 217 pushes the vicinity of the needle tube 3, bending of the distal end 3*d* of the needle tube 3 can be prevented.

<Step S5: Puncture Step>

Figure 15:
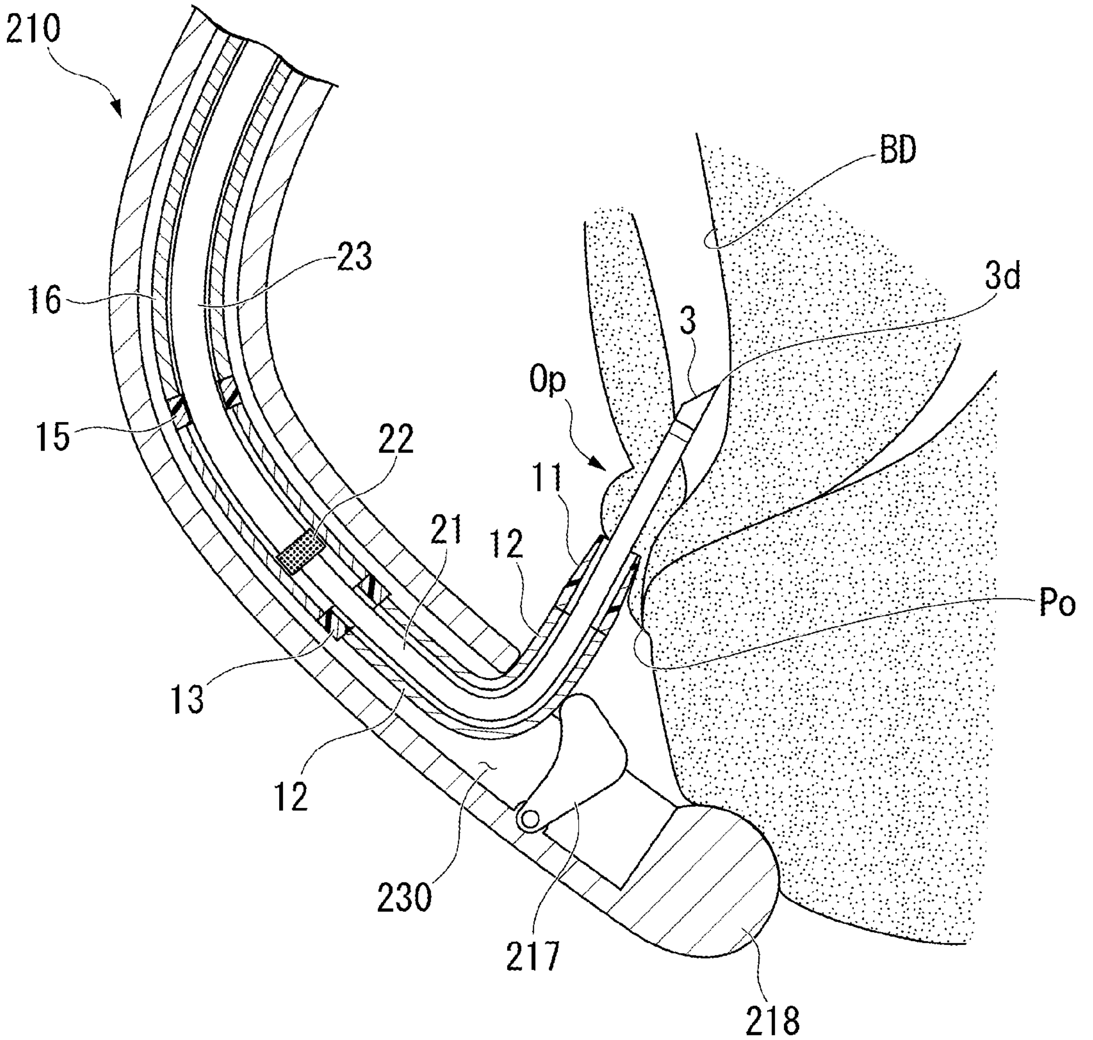
FIG. 15 is a cross-sectional view of the distal end portion of the puncture device in which the needle tube is stuck in the bile duct.

FIG. 15 is a cross-sectional view of the distal end portion of the puncture device 100 with the needle tube 3 stuck in the bile duct BD.

In step S5, the operator operates the operation portion 5 of the puncture device 100 to project the needle tube 3 from the outer sheath 1 under ultrasonic observation. The protruding needle tube 3 sticks into the mouth-side protuberance Op, as shown in FIG. 15. When the needle tube 3 is advanced further, the needle tube 3 approaches the lowest part of the bile duct BD without going out into the abdominal cavity while advancing toward the upstream side of the bile duct BD in the tissue of the oral prominence Op. When the needle tube 3 sticks into the bile duct BD and the distal end 3*d* of the needle tube 3 reaches the inside of the bile duct BD, the operator stops advancing the needle tube 3 and fixes it to the outer sheath 1 so as not to move.

Figure 16:
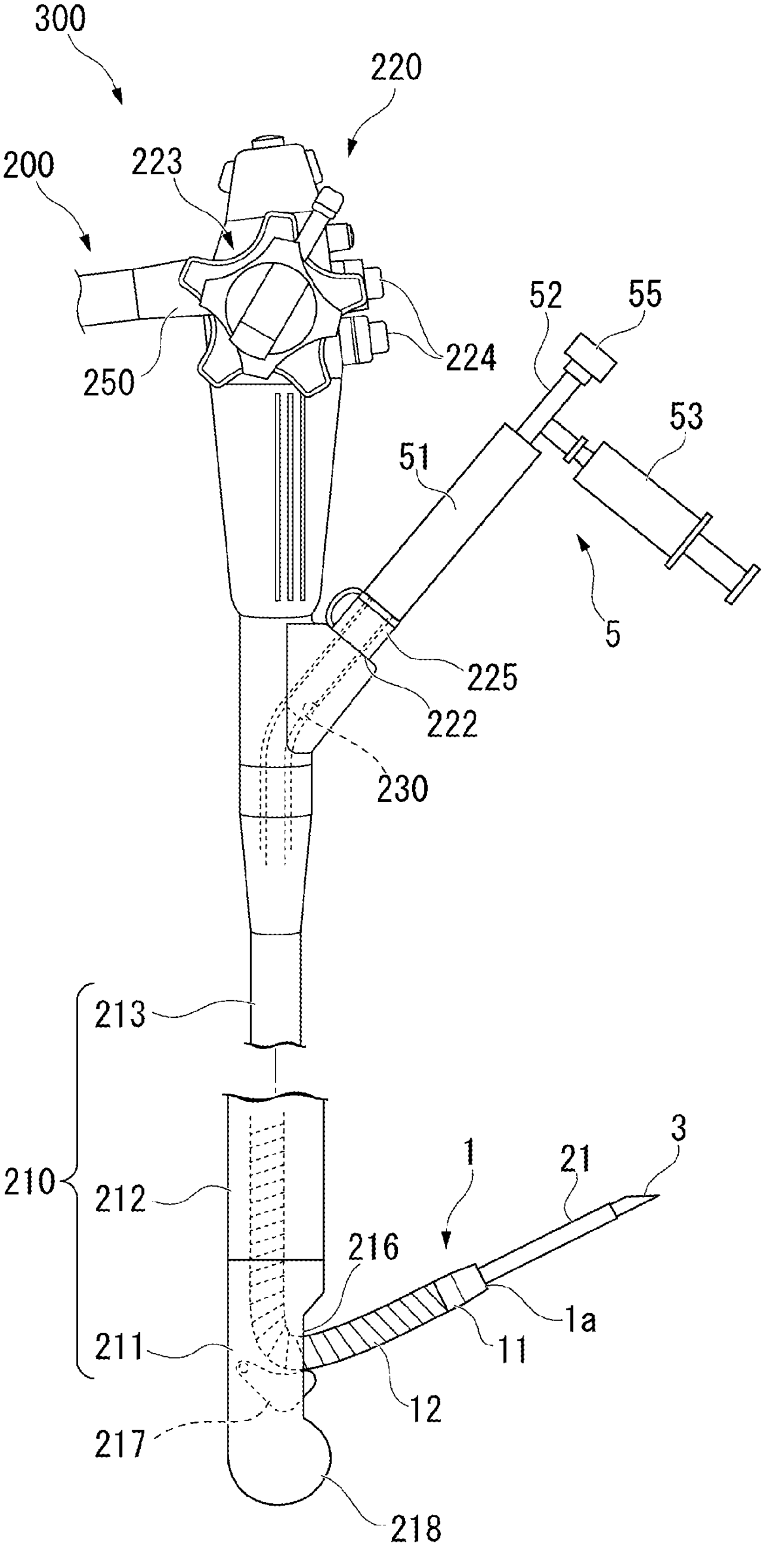
FIG. 16 is a view showing the puncture device with the protruding needle tube.

FIG. 16 is a diagram showing the puncture device 100 with the needle tube 3 protruding.

In the puncture device 100 shown in FIG. 16, the outer sheath 1 is the longest inserted into the treatment instrument channel 230, and the outer sheath 1 protrudes most (fully) from the distal end opening 216 of the endoscope 200. In the puncture device 100 shown in FIG. 16, the inner sheath 2 is arranged at the first position S1 and protrudes most (fully) from the distal end opening 1*a* of the outer sheath 1. That is, the inner sheath 2 shown in FIG. 16 protrudes most (fully) from the distal end opening 216.

Figure 17:
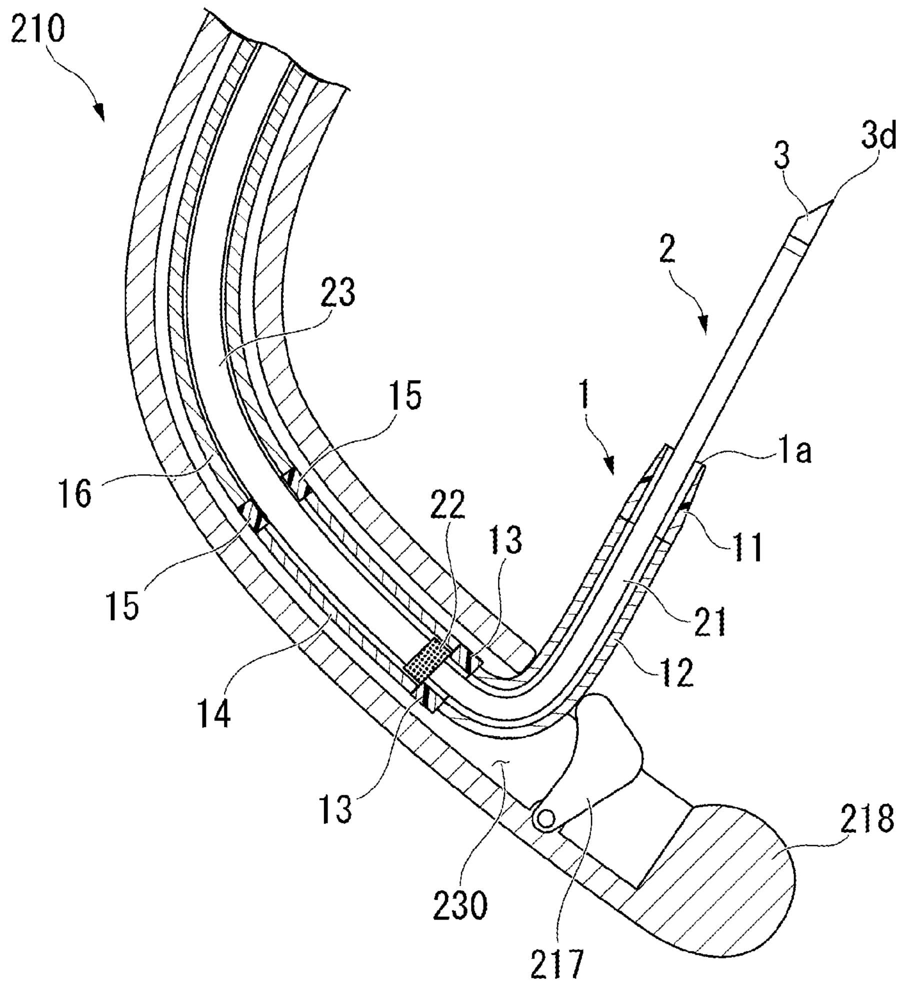
FIG. 17 is a cross-sectional view of the distal end portion of the puncture device in FIG. 16.

FIG. 17 is a cross-sectional view of the distal end portion of puncture device 100 in FIG. 16.

The first connecting portion 13 does not protrude from the distal end opening 216 even when the outer sheath 1 is inserted into the treatment instrument channel 230 for the longest time. At this time, the first connecting portion 13 including the first stopper 13*s* is positioned inside the treatment instrument channel 230, so the proximal end connecting portion 22 including the protrusion 22*t* is positioned inside the treatment instrument channel 230. That is, even when the inner sheath 2 protrudes most (fully) from the distal opening 216, the proximal end connecting portion 22, which is a rigid member, does not protrude from the distal opening 216.

Regardless of the amount of protrusion of the outer sheath 1 and the amount of protrusion of the inner sheath 2, the flexible coil sheath 21 is inserted near the distal end opening 216. So, the operator can easily adjust the position and orientation of the distal end portion 11 of the outer sheath 1 through which the inner sheath 2 is inserted by using the raising base 217. In addition, even when the coil sheath 21, which is prone to bending, is greatly bent by the raising base 217, the coil sheath 21 is less prone to bending.

Since the coil sheath 21 of the inner sheath 2 protrudes from the outer sheath 1 fixed by the raising base 217, it is possible to directly puncture the mouth-side protuberance Op from the positioned position P1. Since the coil sheath 21 is hard to bend, the operator can easily operate the coil sheath 21 in the intended direction.

The maximum amount of protrusion of the inner sheath 2 protruding from the distal end opening 1*a* of the outer sheath 1 may be 10 mm or more, and 20 mm or more.

<Step S6: Imaging Step>

Figure 18:
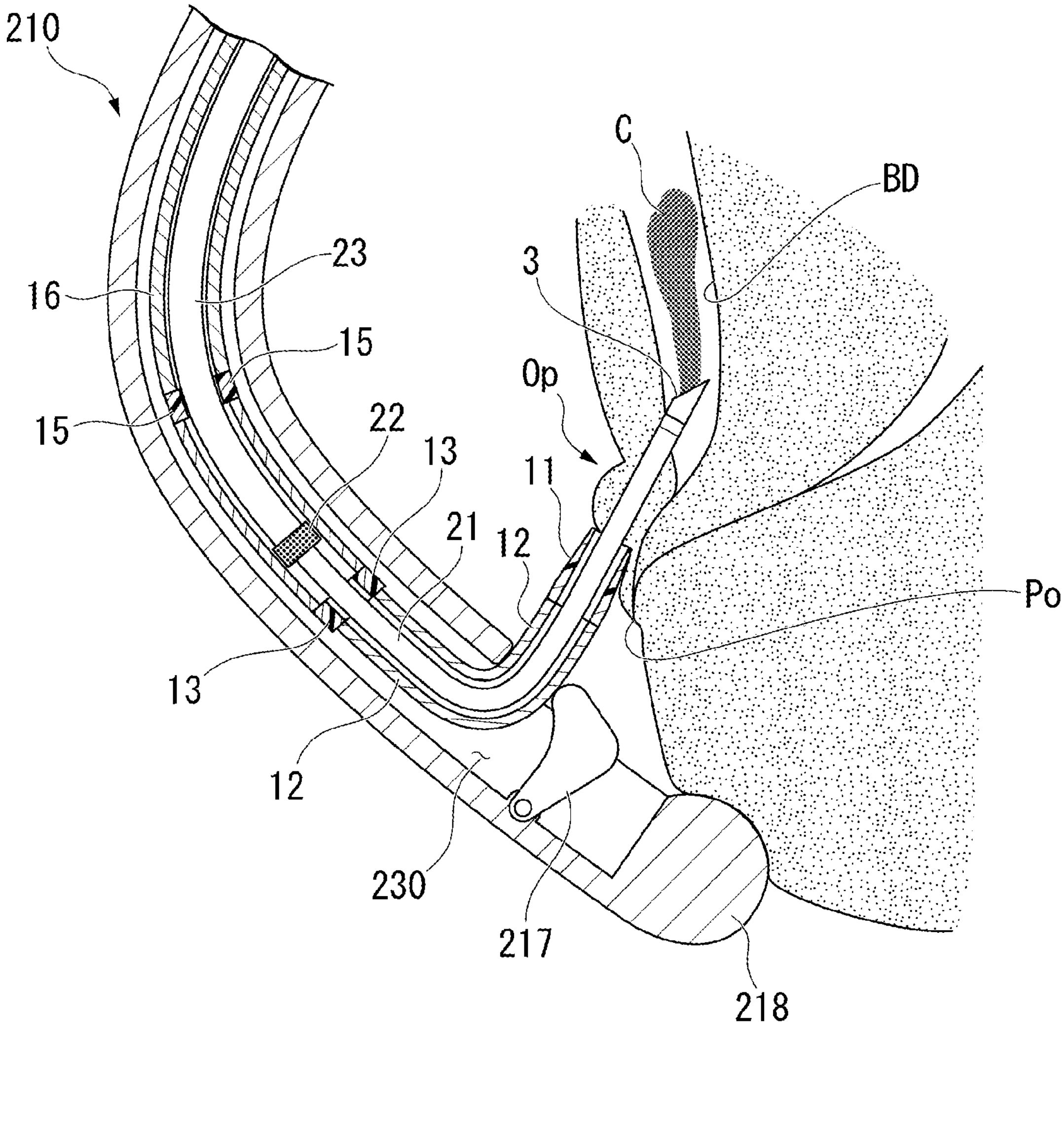
FIG. 18 is a cross-sectional view of the puncture device for pouring a contrast medium.

FIG. 18 is a cross-sectional view of the puncture device 100 into which the contrast medium C is poured.

In step S6, the operator injects the contrast medium C into the syringe 53 to flow the contrast medium C from the puncture device 100 into the bile duct BD. The operator obtains an X-ray image showing the bile duct BD and the like by performing X-ray imaging.

<Step S7: Guide-Wire Insertion Step>

Figure 19:
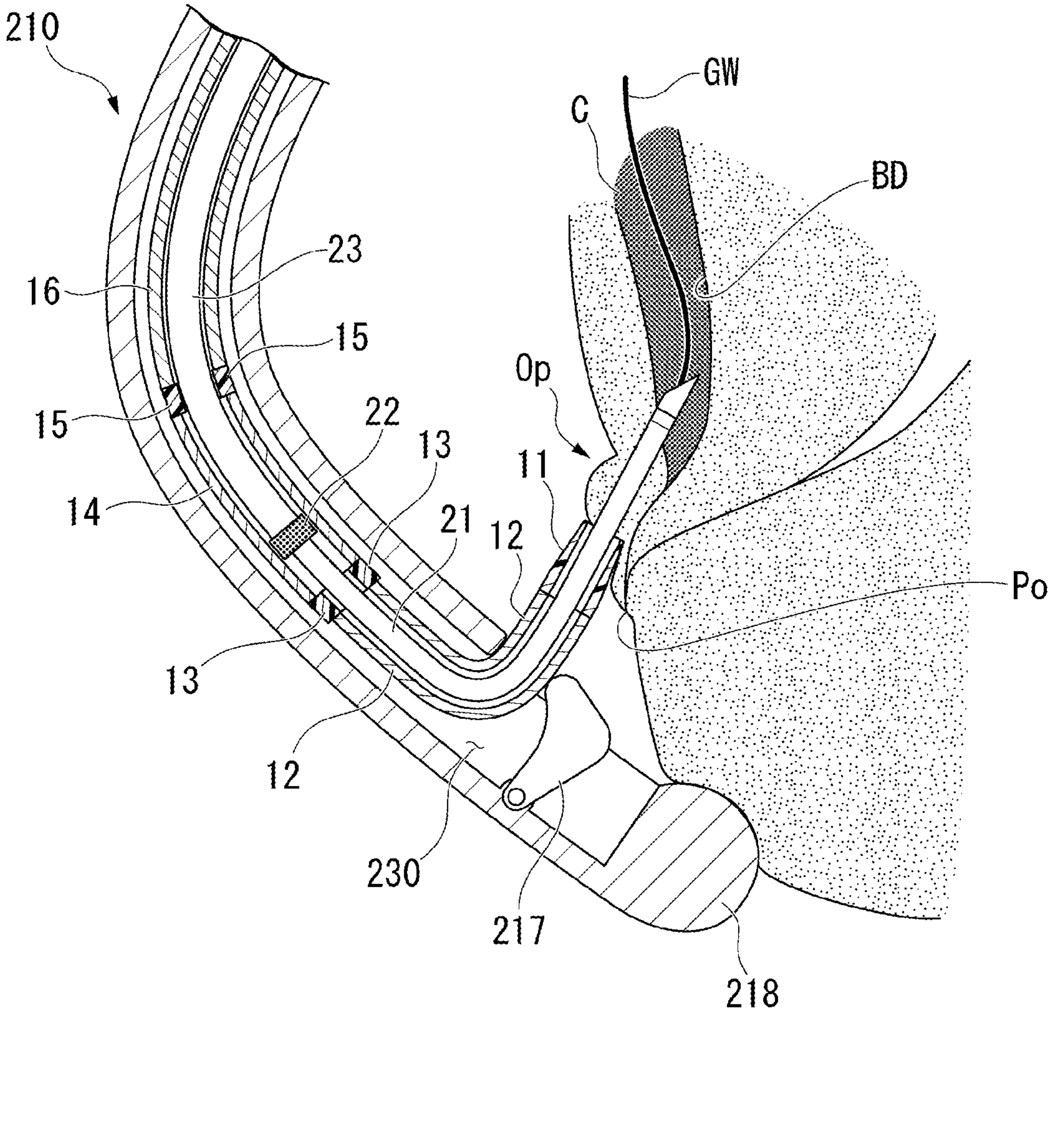
FIG. 19 is a cross-sectional view of the puncture device with a guidewire inserted.

FIG. 19 is a cross-sectional view of the puncture device 100 with the guidewire GW inserted.

In step S7, the operator inserts the guide wire GW into the puncture device 100, protrudes the guide wire GW from the needle tube 3, and inserts the guide wire GW into the bile duct BD. Next, the operator removes the puncture device 100 while leaving the guide wire GW in the bile duct BD. As a result, only the guide wire GW is left in the bile duct BD to form an access route from the duodenum to the bile duct.

After the access route is formed, the operator can perform various treatments by introducing the distal end portions of various treatment instruments along the guide wire GW into the bile duct BD via the access route. Some examples are given below.

Insert an angiography catheter into the bile duct along the guide wire GW, and perform ERCP.

Insert the basket-type instrument along the guide wire GW into the bile duct to treat intrabiliary calculus.

A treatment instrument having a balloon is inserted into the bile duct along the guide wire GW to treat intrabiliary calculi or dilate a narrowed portion of the bile duct.

A biopsy forceps is inserted into the bile duct along the guide wire GW to collect tissue such as the bile duct used for definitive diagnosis of malignant tumors.

A stent delivery system is inserted into the bile duct along the guide wire GW, and a stent (drainage stent) is placed in the bile duct.

When performing the procedure, the access route may be expanded by performing endoscopic papillary sphincterotomy (EST) or endoscopic papillary balloon dilation (EPBD). Furthermore, an access route may be extended by combining EST and EPBD.

According to the puncture device 100 of the present embodiment, the puncture device 100 has both flexibility and rigidity, can be easily bent to the position intended by the operator, and can be easily operated in the direction intended by the operator. Regardless of the amount of protrusion of the outer sheath 1 and the amount of protrusion of the inner sheath 2, the flexible coil sheath (coil sheath 21, distal end coil sheath 12) is inserted near the distal end opening 216, so that the puncture device 100 can be easily bent until the distal end portion is positioned at the duodenal papilla. Since the coil sheath 21 of the inner sheath 2 protrudes from the outer sheath 1 fixed by the raising base 217, the mouth-side protuberance Op can be directly punctured from the positioned position P1.

As described above, the first embodiment of the present disclosure has been described in detail with reference to the drawings, but the specific configuration is not limited to this embodiment, and design changes and the like are included within the scope of the present disclosure. Also, the constituent elements shown in the above-described embodiment and modifications shown below can be combined as appropriate.

(Modification 1)

Figure 20:
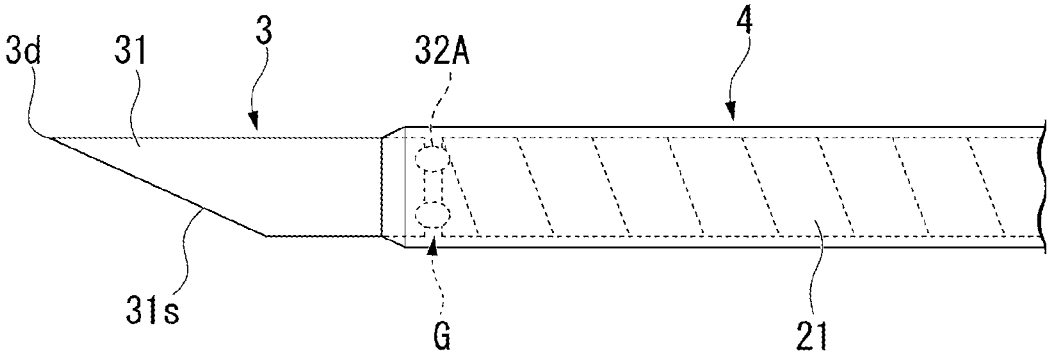
FIG. 20 is a view showing a modification of the distal end connecting portion of the puncture device.
Figure 21:
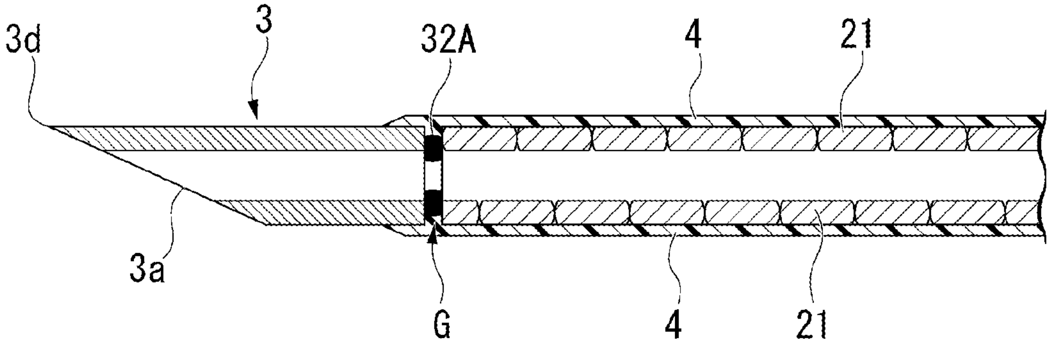
FIG. 21 is a cross-sectional view of the modification of the distal end connecting portion shown in FIG. 20.

In the above embodiment, the distal end connecting portion 32 has steps and unevenness due to connection processing such as laser welding. However, the form of steps and unevenness formed in the distal connecting portion 32 is not limited to this. FIG. 20 is a diagram showing a distal end connecting portion 32A that is a modified example of the distal end connecting portion 32. FIG. 21 is a cross-sectional view of the distal end connecting portion 32A shown in FIG. 20. The cover 4 is provided straddling the distal end connecting portion 32A. The distal end connecting portion 32A is provided in the clearance gap G between the needle tube 3 and the coil sheath 21. That is, the needle tube 3 and the coil sheath 21 are connected by the distal end connecting portion 32A with a gap G provided. The cover 4 is hooked (engaged) on the concave portion of the gap G in the distal connecting portion 32A. Therefore, the cover 4 is fixed to the distal connecting portion 32A and is less likely to slip off the distal connecting portion 32A.

(Modification 2)

Figure 22:
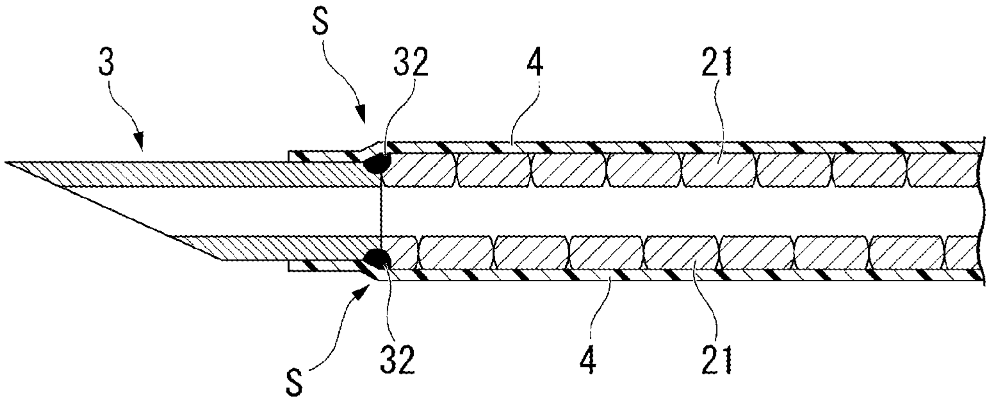
FIG. 22 is a diagram showing another fixing mode of the cover.

In the above-described embodiment, the cover 4 is fixed by being hooked on steps and irregularities caused by connection processing such as laser welding at the distal end connecting portion 32. However, the steps and irregularities to which the cover 4 is fixed are not limited to this. FIG. 22 is a diagram showing another fixing mode of the cover 4. The cover 4 shown in FIG. 22 is hooked and fixed to the step S caused by the difference in outer diameter between the needle tube 3 and the coil sheath 21. The cover 4 is fixed to the step S and is less likely to shift from the step S.

Figure 23:
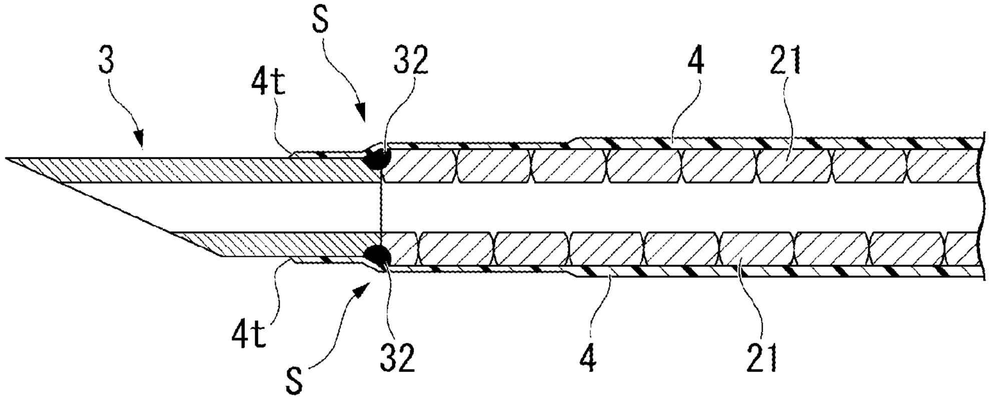
FIG. 23 is a view showing the cover partially melted.

FIG. 23 is a diagram showing the cover 4 partially melted. The cover 4 shown in FIG. 22 may be attached by partially melting in the same manner as the cover 4 shown in FIG. 9. As shown in FIG. 23, the cover 4 attached by melting forms a tapered portion 4*t* at the distal end of the cover 4 by melting. Therefore, the puncture performance of the puncture device 100 is improved.

(Modification 3)

Figure 24:
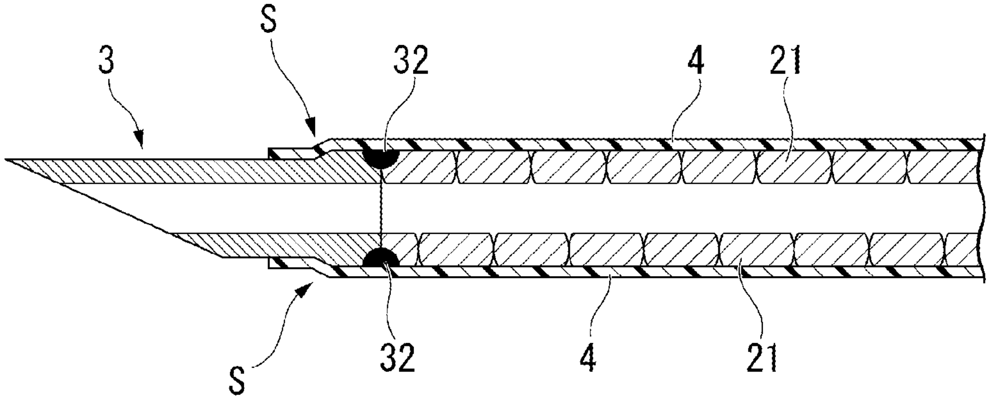
FIG. 24 is a diagram showing another aspect of a step on which the cover is hooked.

FIG. 24 is a diagram showing another aspect of the step S on which the cover 4 is hooked. The cover 4 shown in FIG. 24 is fixed by being hooked on a step S provided on the outer peripheral surface of the needle tube 3 in the vicinity of the distal end connecting portion 32. The cover 4 is fixed to the step S and is less likely to shift from the step S.

(Modification 4)

Figure 25:
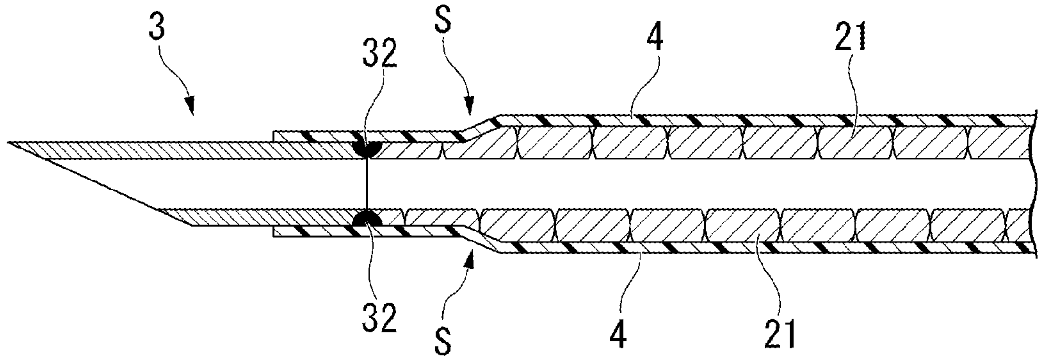
FIG. 25 is a diagram showing another aspect of the step on which the cover is hooked.

FIG. 25 is a diagram showing another aspect of the step S on which the cover 4 is hooked. The cover 4 shown in FIG. 25 is fixed by being hooked on a step S provided on the outer peripheral surface of the coil sheath 21 near the distal end connecting portion 32. The cover 4 is fixed to the step S and is less likely to shift from the step S.

Figure 26:
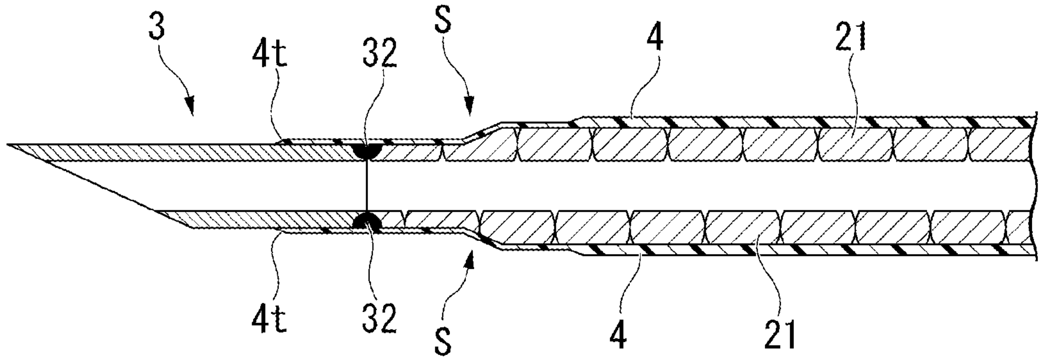
FIG. 26 is a view showing the cover partially melted.

FIG. 26 is a diagram showing the cover 4 partially melted. The cover 4 shown in FIG. 25 may be attached by partially melting in the same manner as the cover 4 shown in FIG. 9. As shown in FIG. 26, the cover 4 attached by melting forms a tapered portion 4*t* at the distal end of the cover 4 by melting. Therefore, the puncture performance of the puncture device 100 is improved.

(Modification 7)

Figure 27:
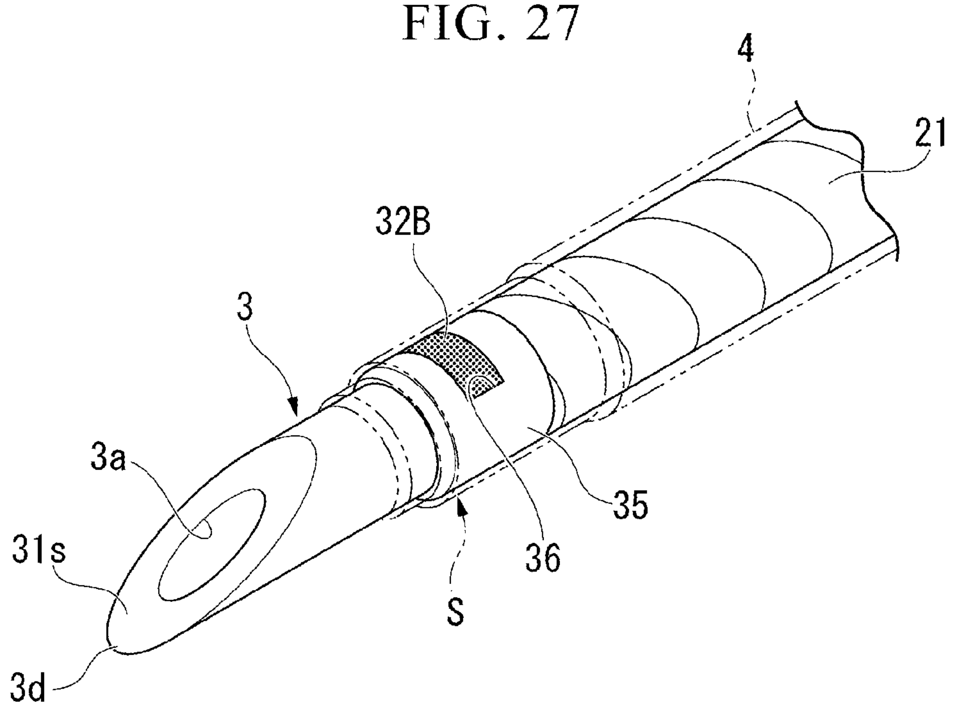
FIG. 27 is a diagram showing another modified example of the distal end connecting portion.
Figure 28:
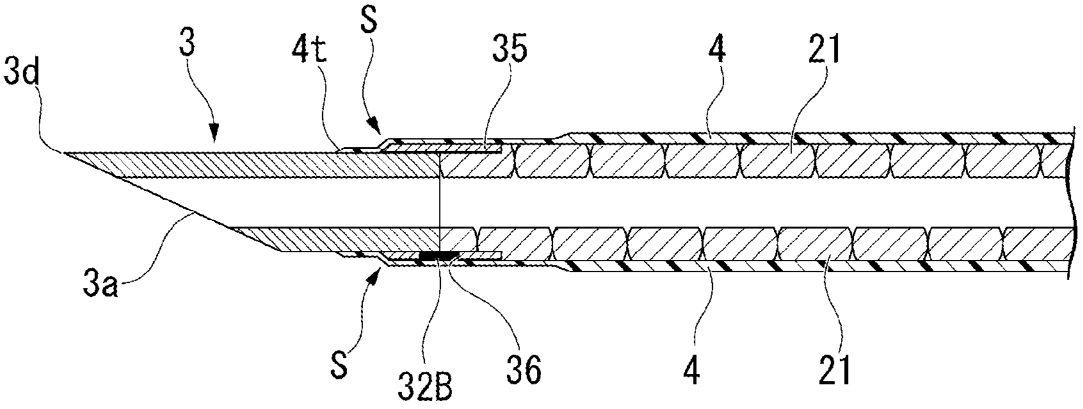
FIG. 28 is a cross-sectional view of the modification of the distal end connecting portion shown in FIG. 27.

In the above-described embodiment, the cover 4 is fixed by being hooked on steps and irregularities caused by connection processing such as laser welding at the distal end connecting portion 32. However, the steps and irregularities to which the cover 4 is fixed are not limited to this. FIG. 27 is a diagram showing a distal end connecting portion 32B that is a modified example of the distal end connecting portion 32. FIG. 28 is a cross-sectional view of the distal end connecting portion 32B shown in FIG. 27. The needle tube 3 and the coil sheath 21 are connected via a connecting pipe 35. The connection pipe 35 is provided with an opening 36 for brazing. The distal end connecting portion 32B is formed by brazing injected from the opening 36 for brazing. The cover 4 is provided across the distal end connecting portion 32B. The cover 4 shown in FIG. 27 is fixed by being hooked on a step S provided on the distal end side A1 of the connection pipe 35 near the distal end connecting portion 32B. The cover 4 is fixed to the step S and is less likely to shift from the step S.

(Modification 8)

Figure 29:
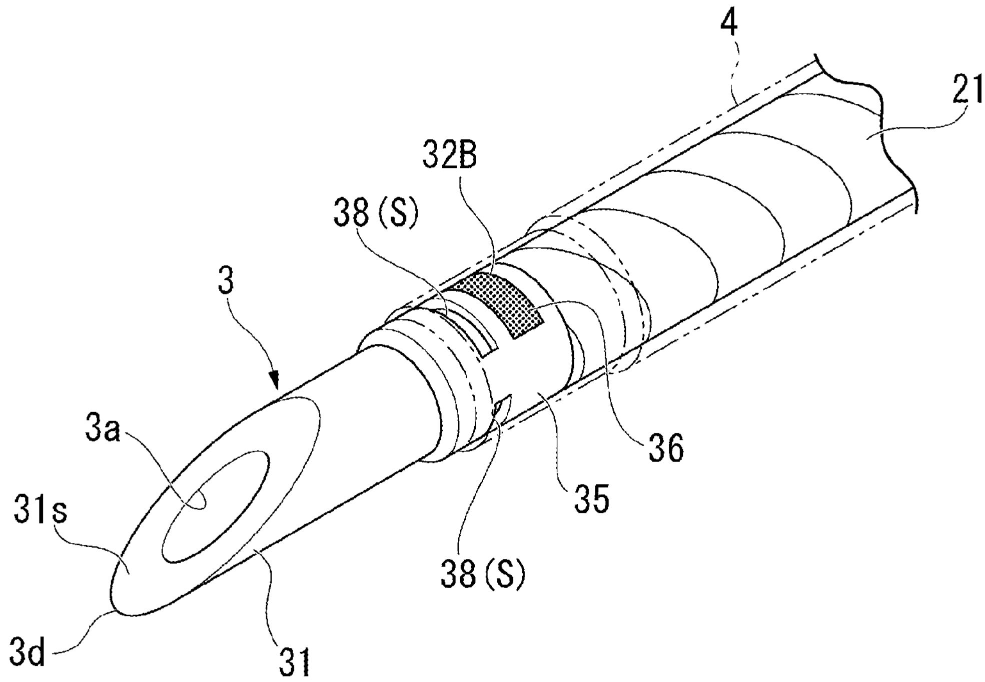
FIG. 29 is a diagram showing another aspect of a step on which the cover is hooked.
Figure 30:
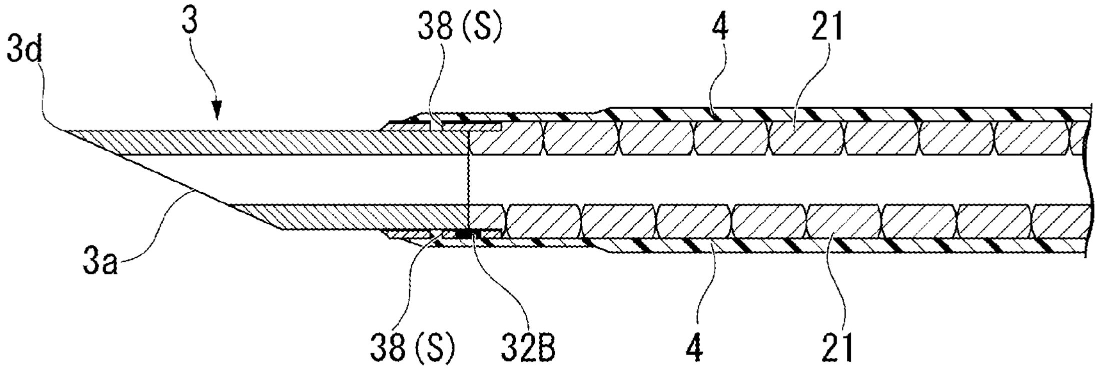
FIG. 30 is a cross-sectional view of the distal end connecting portion shown in FIG. 29.

FIG. 29 is a diagram showing another aspect of the step S on which the cover 4 is hooked. FIG. 30 is a cross-sectional view of the distal end connecting portion 32B shown in FIG. 29. The cover 4 shown in FIG. 29 is fixed by being caught on a step S formed by a hooking hole 38 provided near the tip connecting portion 32B and on the distal end side A1 of the outer circumferential surface of the connecting pipe 35 rather than the brazing opening 36. The cover 4 is fixed to the step S and is less likely to shift from the step S.

What is claimed is:

1. A puncture device inserted into an endoscope channel, comprising:

an outer sheath; and an inner sheath inserted into the outer sheath, the inner sheath including;

a coil sheath; and a needle tube located at a distal end of the coil sheath;

a connecting portion connecting the needle tube and the coil sheath; and a proximal sheath located proximally relative to the coil sheath;

wherein the outer sheath includes:

a first stopper fixing the inner sheath at a first position where the inner sheath is fully advanced relative to the outer sheath; and a second stopper fixing the inner sheath at a second position where the inner sheath is fully retracted relative to the outer sheath;

wherein the inner sheath further includes:

a proximal end connecting portion connecting the coil sheath and the proximal sheath, the proximal end connecting portion including a protrusion engaging with the first stopper and the second stopper.

2. The puncture device according to claim 1, wherein the inner sheath further includes a cover covering the coil sheath and the connecting portion, and wherein the cover is engaged on an unevenness formed on the connecting portion.

3. The puncture device according to claim 1, wherein the inner sheath further includes a cover covering the coil sheath and the connecting portion, and wherein the cover is engaged on a step formed from the needle tube to the coil sheath.

4. The puncture device according to claim 1, wherein the inner sheath further includes a cover covering the coil sheath and the connecting portion, and wherein the connecting portion includes a part connected by laser welding, and wherein the cover is caught on one or more welding marks by the laser welding.

5. The puncture device according to claim 1, wherein the inner sheath further includes a cover covering the coil sheath and the connecting portion, and wherein the cover includes a heat-shrinkable tube.

6. The puncture device according to claim 1, wherein the inner sheath further includes a cover covering the coil sheath and the connecting portion, and wherein the needle tube includes a concave portion with a recessed outer surface, and wherein the cover covers the concave portion.

7. The puncture device according to claim 1, wherein the inner sheath further includes a cover covering the coil sheath and the connecting portion, and wherein the needle tube includes a concave portion with a recessed outer surface, and wherein the cover is engaged on the concave portion.

8. The puncture device according to claim 1, wherein the inner sheath further includes a cover covering the coil sheath and the connecting portion, wherein when the inner sheath is arranged at the first position, the needle tube protrudes from the outer sheath, and wherein when the inner sheath is arranged at the second position, the needle tube is accommodated in the outer sheath.

9. The puncture device according to claim 8, wherein the outer sheath includes a rigid tube at the distal end, and wherein when the inner sheath is arranged at the second position, the distal end of the needle tube is arranged at a position surrounded by the rigid tube.

10. The puncture device according to claim 8, wherein the outer sheath includes:
- a distal end coil sheath located at the distal end of the outer sheath;
- an intermediate coil sheath located on a proximal side of the distal end coil sheath;
- a proximal end coil sheath located on a proximal side of the intermediate coil sheath;
- a first connecting portion connecting the distal end coil sheath and the intermediate coil sheath; and
- a second connecting portion connecting the intermediate coil sheath and the proximal end coil sheath, wherein the first connecting portion is located on the first stopper, and wherein the second connecting portion is located on the second stopper.

11. The puncture device according to claim 10, wherein the distal end coil sheath is made of a flat wire thinner than the proximal end coil sheath.

12. The puncture device according to claim 10, wherein a length from the first stopper to a proximal opening of the outer sheath is shorter than a length of the channel of the endoscope.

13. The puncture device according to claim 1, wherein the proximal sheath is made of resin.

14. An endoscopy system, comprising:
- an endoscope having a channel through which a puncture device is inserted, the puncture device, including:
  - an outer sheath; and
  - an inner sheath inserted into the outer sheath, the inner sheath including:
    - a coil sheath;
    - a needle tube located at a distal end of the coil sheath;
    - a connecting portion connecting the needle tube and the coil sheath; and
    - a cover covering the coil sheath and the connecting portion;
  - wherein the outer sheath includes:
    - a distal end coil sheath located at a distal end of the outer sheath;
    - an intermediate coil sheath located on a proximal side of the distal end coil sheath;
    - a proximal end coil sheath located on a proximal side of the intermediate coil sheath;
    - a first connecting portion connecting the distal end coil sheath and the intermediate coil sheath; and
    - a second connecting portion connecting the intermediate coil sheath and the proximal end coil sheath; wherein the first connecting portion includes a first stopper fixing the inner sheath at a first position where the inner sheath is fully advanced relative to the outer sheath, wherein the second connecting portion includes a second stopper fixing the inner sheath at a second position where the inner sheath is fully retracted relative to the outer sheath, and wherein a length from the first stopper to a proximal opening of the outer sheath is shorter than a length of the channel of the endoscope.

15. The endoscopy system according to claim 14, wherein when the inner sheath is arranged at the first position, the needle tube protrudes from the outer sheath, and wherein when the inner sheath is arranged at the second position, the needle tube is accommodated in the outer sheath.

16. The endoscopy system according to claim 14, wherein the distal end coil sheath is made of a flat wire that is thinner than the proximal end coil sheath.

17. The endoscopy system according to claim 14, wherein when the inner sheath is arranged at the second position, the needle tube is accommodated in the outer sheath.

18. The endoscopy system according to claim 14, wherein the inner sheath further includes:
- a proximal sheath located on a proximal side of the coil sheath; and
- a proximal end connecting portion connecting the coil sheath and the proximal sheath, the proximal end connecting portion including a protrusion engaging with the first stopper and the second stopper.

19. The endoscopy system according to claim 14, wherein the outer sheath further includes a rigid tube-shaped protective member at the distal end of the distal end coil sheath, and wherein when the inner sheath is arranged at the second position, the distal end of the needle tube is arranged at a position surrounded by the rigid tube-shaped protective member.

* * * * *